United States Patent [19]

Higgins et al.

[11] Patent Number: 4,935,237
[45] Date of Patent: Jun. 19, 1990

[54] PROCESSES FOR THE PREPARATION OF T-PA MUTANTS

[75] Inventors: Deborah L. Higgins, San Mateo; William E. Holmes, Pacifica; Adair J. Hotchkiss, Half Moon Bay, all of Calif.

[73] Assignee: Genentech, Inc., S. San Francisco, Calif.

[21] Appl. No.: 188,237

[22] Filed: Apr. 29, 1988

Related U.S. Application Data

[63] Continuation of Ser. No. 170,970, Mar. 21, 1988, abandoned, and a continuation of Ser. No. 68,448, Jun. 30, 1987, abandoned.

[51] Int. Cl.$^5$ ............... A61K 37/547; C12N 9/50; C12N 9/64
[52] U.S. Cl. ............... 424/94.64; 424/94.63; 435/219; 435/226; 435/69.1; 435/172.3; 935/14
[58] Field of Search ............... 424/94.63, 94.64; 435/212, 215, 217, 172.3, 69.1, 219, 226; 935/14

[56] References Cited

FOREIGN PATENT DOCUMENTS 0196920 10/1986 European Pat. Off. .
0207589 1/1987 European Pat. Off. .
8704722 8/1987 PCT Int'l Appl. .
2119804 11/1983 United Kingdom ............... 435/212
8401786 5/1984 World Int. Prop. O. .

OTHER PUBLICATIONS

Collen et al, Circ. vol. 70, No. 6, Dec. 1984, pp. 1012–1017.
Kagitani et al, FEBS Letters, vol. 189, No. 1, Sep. 1985, pp. 145–149.
Rijken et al, Biochem. J. vol. 238, 1986, pp. 643–646.
Tate et al, Biochemistry, vol. 26, No. 2, Jan. 1987, pp. 338–343.
Browne, et al., *J. Biol. Chem.* 263 #4, 1599 (1988).
Kalyan et al., J. Biol. Chem. 263 #8, 3971 (1988).

*Primary Examiner*—Jacqueline Stone
*Attorney, Agent, or Firm*—Walter H. Dreger

[57] ABSTRACT

Disclosed herein are improved processes for preparing variant human t-PA proteins exhibiting improved pharmacokinetic properties relative to natural t-PA. One such illustrated variant, devoid of amino acids corresponding to amino acids 1 through 44 of natural t-PA, is shown to exhibit a plasma half-life of greater than about 15 times the plasma half-file of natural t-PA, as well as a clearance rate of less than about 1/10 the clearance rate of natural t-PA. Also disclosed are improved processes for treating vascular disease employing pharmaceutical compositions which incorporate therapeutically effective amounts of such t-PA variants with pharmaceutically acceptable diluents or excipients.

15 Claims, 19 Drawing Sheets

```
GTTCTGAGCACAGGGCTGGAGAGAAAACCTCTGCGAGGAAAGGGAAGGAGCAAGCCGTGA
```

```
                                          -35                    -30
                                          met asp ala met lys arg gly leu
            ATTTAAGGGACGCTGTGAAGCAATC     ATG GAT GCA ATG AAG AGA GGG CTC -20
cys cys val leu leu leu cys      gly ala val phe val ser pro ser
TGC TGT GTG CTG CTG CTG TGT      GGA GCA GTC TTC GTT TCG CCC AGC -10                                          1
gln glu ile his ala arg phe arg arg gly ala arg         SER TYR GLN
CAG GAA ATC CAT GCC CGA TTC AGA AGA GGA GCC AGA         TCT TAC CAA 10
VAL ILE CYS ARG ASP GLU LYS THR GLN MET ILE TYR GLN GLN HIS
GTG ATC TGC AGA GAT GAA AAA ACG CAG ATG ATA TAC CAG CAA CAT 20                                       30
GLN SER TRP LEU ARG PRO VAL LEU ARG SER ASN ARG VAL GLU TYR
CAG TCA TGG CTG CGC CCT GTG CTC AGA AGC AAC CGG GTG GAA TAT 40
CYS TRP CYS ASN SER GLY ARG ALA GLN CYS HIS SER VAL PRO VAL
TGC TGG TGC AAC AGT GGC AGG GCA CAG TGC CAC TCA GTG CCT GTC 50                                       60
LYS SER CYS SER GLU PRO ARG CYS PHE ASN GLY GLY THR CYS GLN
AAA AGT TGC AGC GAG CCA AGG TGT TTC AAC GGG GGC ACC TGC CAG 70
GLN ALA LEU TYR PHE SER ASP PHE VAL CYS GLN CYS PRO GLU GLY
CAG GCC CTG TAC TTC TCA GAT TTC GTG TGC CAG TGC CCC GAA GGA 80                                       90
PHE ALA GLY LYS CYS CYS GLU ILE ASP THR ARG ALA THR CYS TYR
TTT GCT GGG AAG TGC TGT GAA ATA GAT ACC AGG GCC ACG TGC TAC 100
GLU ASP GLN GLY ILE SER TYR ARG GLY THR TRP SER THR ALA GLU
GAG GAC CAG GGC ATC AGC TAC AGG GGC ACG TGG AGC ACA GCG GAG 110                                      120
SER GLY ALA GLU CYS THR ASN TRP ASN SER SER ALA LEU ALA GLN
AGT GGC GCC GAG TGC ACC AAC TGG AAC AGC AGC GCG TTG GCC CAG 130
LYS PRO TYR SER GLY ARG ARG PRO ASP ALA ILE ARG LEU GLY LEU
AAG CCC TAC AGC GGG CGG AGG CCA GAC GCC ATC AGG CTG GGC CTG 140                                      150
GLY ASN HIS ASN TYR CYS ARG ASN PRO ASP ARG ASP SER LYS PRO
GGG AAC CAC AAC TAC TGC AGA AAC CCA GAT CGA GAC TCA AAG CCC 160
TRP CYS TYR VAL PHE LYS ALA GLY LYS TYR SER SER GLU PHE CYS
TGG TGC TAC GTC TTT AAG GCG GGG AAG TAC AGC TCA GAG TTC TGC 170                                      180
SER THR PRO ALA CYS SER GLU GLY ASN SER ASP CYS TYR PHE GLY
AGC ACC CCT GCC TGC TCT GAG GGA AAC AGT GAC TGC TAC TTT GGG
```

FIG. IA

```
                                190
ASN GLY SER ALA TYR ARG GLY THR HIS SER LEU THR GLU SER GLY
AAT GGG TCA GCC TAC CGT GGC ACG CAC AGC CTC ACC GAG TCG GGT 200                                         210
ALA SER CYS LEU PRO TRP ASN SER MET ILE LEU ILE GLY LYS VAL
GCC TCC TGC CTC CCG TGG AAT TCC ATG ATC CTG ATA GGC AAG GTT

220
TYR THR ALA GLN ASN PRO SER ALA GLN ALA LEU GLY LEU GLY LYS
TAC ACA GCA CAG AAC CCC AGT GCC CAG GCA CTG GGC CTG GGC AAA 230                                     240
HIS ASN TYR CYS ARG ASN PRO ASP GLY ASP ALA LYS PRO TRP CYS
CAT AAT TAC TGC CGG AAT CCT GAT GGG GAT GCC AAG CCC TGG TGC

250
HIS VAL LEU LYS ASN ARG ARG LEU THR TRP GLU TYR CYS ASP VAL
CAC GTG CTG AAG AAC CGC AGG CTG ACG TGG GAG TAC TGT GAT GTG 260                                         270
PRO SER CYS SER THR CYS GLY LEU ARG GLN TYR SER GLN PRO GLN
CCC TCC TGC TCC ACC TGC GGC CTG AGA CAG TAC AGC CAG CCT CAG

280
PHE ARG ILE LYS GLY GLY LEU PHE ALA ASP ILE ALA SER HIS PRO
TTT CGC ATC AAA GGA GGG CTC TTC GCC GAC ATC GCC TCC CAC CCC 290                                     300
TRP GLN ALA ALA ILE PHE ALA LYS HIS ARG ARG SER PRO GLY GLU
TGG CAG GCT GCC ATC TTT GCC AAG CAC AGG AGG TCG CCC GGA GAG

310
ARG PHE LEU CYS GLY GLY ILE LEU ILE SER SER CYS TRP ILE LEU
CGG TTC CTG TGC GGG GGC ATA CTC ATC AGC TCC TGC TGG ATT CTC 320                                         330
SER ALA ALA HIS CYS PHE GLN GLU ARG PHE PRO PRO HIS HIS LEU
TCT GCC GCC CAC TGC TTC CAG GAG AGG TTT CCG CCC CAC CAC CTG

340
THR VAL ILE LEU GLY ARG THR TYR ARG VAL VAL PRO GLY GLU GLU
ACG GTG ATC TTG GGC AGA ACA TAC CGG GTG GTC CCT GGC GAG GAG 350                                     360
GLU GLN LYS PHE GLU VAL GLU LYS TYR ILE VAL HIS LYS GLU PHE
GAG CAG AAA TTT GAA GTC GAA AAA TAC ATT GTC CAT AAG GAA TTC

370
ASP ASP ASP THR TYR ASP ASN ASP ILE ALA LEU LEU GLN LEU LYS
GAT GAT GAC ACT TAC GAC AAT GAC ATT GCG CTG CTG CAG CTG AAA 380                                     390
SER ASP SER SER ARG CYS ALA GLN GLU SER SER VAL VAL ARG THR
TCG GAT TCG TCC CGC TGT GCC CAG GAG AGC AGC GTG GTC CGC ACT

400
VAL CYS LEU PRO PRO ALA ASP LEU GLN LEU PRO ASP TRP THR GLU
GTG TGC CTT CCC CCG GCG GAC CTG CAG CTG CCG GAC TGG ACG GAG 410                                     420
CYS GLU LEU SER GLY TYR GLY LYS HIS GLU ALA LEU SER PRO PHE
TGT GAG CTC TCC GGC TAC GGC AAG CAT GAG GCC TTG TCT CCT TTC
```

FIG. 1B

```
                                430
TYR SER GLU ARG LEU LYS GLU ALA HIS VAL ARG LEU TYR PRO SER
TAT TCG GAG CGG CTG AAG GAG GCT CAT GTC AGA CTG TAC CCA TCC 440                                     450
SER ARG CYS THR SER GLN HIS LEU LEU ASN ARG THR VAL THR ASP
AGC CGC TGC ACA TCA CAA CAT TTA CTT AAC AGA ACA GTC ACC GAC

460
ASN MET LEU CYS ALA GLY ASP THR ARG SER GLY GLY PRO GLN ALA
AAC ATG CTG TGT GCT GGA GAC ACT CGG AGC GGC GGG CCC CAG GCA 470                                 480
ASN LEU HIS ASP ALA CYS GLN GLY ASP SER GLY GLY PRO LEU VAL
AAC TTG CAC GAC GCC TGC CAG GGC GAT TCG GGA GGC CCC CTG GTG

490
CYS LEU ASN ASP GLY ARG MET THR LEU VAL GLY ILE ILE SER TRP
TGT CTG AAC GAT GGC CGC ATG ACT TTG GTG GGC ATC ATC AGC TGG 500                                         510
GLY LEU GLY CYS GLY GLN LYS ASP VAL PRO GLY VAL TYR THR LYS
GGC CTG GGC TGT GGA CAG AAG GAT GTC CCG GGT GTG TAC ACC AAG 520                     527
VAL THR ASN TYR LEU ASP TRP ILE ARG ASP ASN MET ARG PRO OP
GTT ACC AAC TAC CTA GAC TGG ATT CGT GAC AAC ATG CGA CCG TGA

CCAGGAACACCCGACTCCTCAAAAGCAAATGAGATCCCGCCTCTTCTTCTTCAGAAGACA

CTGCAAAGGCGCAGTGCTTCTCTACAGACTTCTCCAGACCCACCACACCGCAGAAGCGGG

ACGAGACCCTACAGGAGAGGGAAGAGTGCATTTTCCCAGATACTTCCCATTTTGGAAGT

TTTCAGGACTTGGTCTGATTTCAGGATACTCTGTCAGATGGGAAGACATGAATGCACACT

AGCCTCTCCAGGAATGCCTCCTCCCTGGGCAGAAAGTGGCCATGCCACCCTGTTTTCAGCTA

AAGCCCAACCTCCTGACCTGTCACCGTGAGCAGCTTTGGAAACAGGACCACAAAAATGAA

AGCATGTCTCAATAGTAAAAGATAACAAGATCTTTCAGGAAAGACGGATTGCATTAGAA

ATAGACAGTATATTTATAGTCACAAGAGCCCAGCAGGGCCTCAAAGTTGGGGCAGGCTGGC

TGGCCCGTCATGTTCCTCAAAAGCACCCTTGACGTCAAGTCTCCTTCCCCTTTCCCCACT

CCCTGGCTCTCAGAAGGTATTCCTTTTGTGTACAGTGTGTAAAGTGTAAATCCTTTTTCT

TTATAAACTTTAGAGTAGCATGAGAGAATTGTATCATTTGAACAACTAGGCTTCAGCATA

TTTATAGCAATCCATGTTAGTTTTTACTTTCTGTTGCCACAACCCTGTTTTATACTGTA

CTTAATAAATTCAGATATATTTTTCACAGTTTTTCCAAAAAAAAAAAAAAA
```

FIG. IC

```
                          -30                                        -20
        MetAspAlaMetLysArgGlyLeuCysCysValLeuLeuLeuCysGlyAlaValPheVal
      1 ATGGATGCAATGAAGAGAGGGCTCTGCTGTGTGCTGCTGCTGTGTGGAGCAGTCTTCGTT

-10                                   -1 45
        SerProSerGlnGluIleHisAlaArgPheArgArgGlyAlaArgSerValProValLys
        TCGCCCAGCCAGGAAATCCATGCCCGATTCAGAAGAGGAGCCAGATCTGTGCCTGTCAAA 50                                      60
        SerCysSerGluProArgCysPheAsnGlyGlyThrCysGlnGlnAlaLeuTyrPheSer
    121 AGTTGCAGCGAGCCAAGGTGTTTCAACGGGGGCACCTGCCAGCAGGCCCTGTACTTCTCA 70                                      80
        AspPheValCysGlnCysProGluGlyPheAlaGlyLysCysCysGluIleAspThrArg
        GATTTCGTGTGCCAGTGCCCCGAAGGATTTGCTGGGAAGTGCTGTGAAATAGATACCAGG 90                                      100
        AlaThrCysTyrGluAspGlnGlyIleSerTyrArgGlyThrTrpSerThrAlaGluSer
    241 GCCACGTGCTACGAGGACCAGGGCATCAGCTACAGGGGCACGTGGAGCACAGCGGAGAGT 110                                     120
        GlyAlaGluCysThrAsnTrpAsnSerSerAlaLeuAlaGlnLysProTyrSerGlyArg
        GGCGCCGAGTGCACCAACTGGAACAGCAGCGCGTTGGCCCAGAAGCCCTACAGCGGGCGG 130                                     140
        ArgProAspAlaIleArgLeuGlyLeuGlyAsnHisAsnTyrCysArgAsnProAspArg
    361 AGGCCAGACGCCATCAGGCTGGGCCTGGGGAACCACAACTACTGCAGAAACCCAGATCGA
```

FIG. 12-1

```
          150                              160
    AspSerLysProTrpCysTyrValPheLysAlaGlyLysTyrSerSerGluPheCysSer
    GACTCAAAGCCCTGGTGCTACGTCTTTAAGGCGGGGAAGTACAGCTCAGAGTTCTGCAGC 170                              180
    ThrProAlaCysSerGluGlyAsnSerAspCysTyrPheGlyAsnGlySerAlaTyrArg
481 ACCCCTGCCTGCTCTGAGGGAAACAGTGACTGCTACTTTGGGAATGGGTCAGCCTACCGT 190                              200
    GlyThrHisSerLeuThrGluSerGlyAlaSerCysLeuProTrpAsnSerMetIleLeu
    GGCACGCACAGCCTCACCGAGTCGGGTGCCTCCTGCCTCCCGTGGAATTCCATGATCCTG 210                              220
    IleGlyLysValTyrThrAlaGlnAsnProSerAlaGlnAlaLeuGlyLeuGlyLysHis
601 ATAGGCAAGGTTTACACAGCACAGAACCCCAGTGCCCAGGCACTGGGCCTGGGCAAACAT 230                              240
    AsnTyrCysArgAsnProAspGlyAspAlaLysProTrpCysHisValLeuLysAsnArg
    AATTACTGCCGGAATCCTGATGGGGATGCCAAGCCCTGGTGCCACGTGCTGAAGAACCGC 250                              260
    ArgLeuThrTrpGluTyrCysAspValProSerCysSerThrCysGlyLeuArgGlnTyr
721 AGGCTGACGTGGGAGTACTGTGATGTGCCCTCCTGCTCCACCTGCGGCCTGAGACAGTAC 270                              280
    SerGlnProGlnPheGluIleLysGlyGlyLeuPheAlaAspIleAlaSerHisProTrp
    AGCCAGCCTCAGTTTGAAATCAAAGGAGGGCTCTTCGCCGACATCGCCTCCCACCCCTGG 290                              300
    GlnAlaAlaIlePheAlaLysHisArgArgSerProGlyGluArgPheLeuCysGlyGly
841 CAGGCTGCCATCTTTGCCAAGCACAGGAGGTCGCCCGGAGAGCGGTTCCTGTGCGGGGGC
```

FIG. 12-2

```
          310                          320
     IleLeuIleSerSerCysTrpIleLeuSerAlaAlaHisCysPheGlnGluArgPhePro
     ATACTCATCAGCTCCTGCTGGATTCTCTCTGCCGCCCACTGCTTCCAGGAGAGGTTTCCG 330                          340
     ProHisHisLeuThrValIleLeuGlyArgThrTyrArgValValProGlyGluGluGlu
961  CCCCACCACCTGACGGTGATCTTGGGCAGAACATACCGGGTGGTCCCTGGCGAGGAGGAG 350                          360
     GlnLysPheGluValGluLysTyrIleValHisLysGluPheAspAspAspThrTyrAsp
     CAGAAATTTGAAGTCGAAAAATACATTGTCCATAAGGAATTCGATGATGACACTTACGAC 370                          380
     AsnAspIleAlaLeuLeuGlnLeuLysSerAspSerSerArgCysAlaGlnGluSerSer
1081 AATGACATTGCGCTGCTGCAGCTGAAATCGGATTCGTCCCGCTGTGCCCAGGAGAGCAGC 390                          400
     ValValArgThrValCysLeuProProAlaAspLeuGlnLeuProAspTrpThrGluCys
     GTGGTCCGCACTGTGTGCCTTCCCCCGGCGGACCTGCAGCTGCCGGACTGGACGGAGTGT 410                          420
     GluLeuSerGlyTyrGlyLysHisGluAlaLeuSerProPheTyrSerGluArgLeuLys
1201 GAGCTCTCCGGCTACGGCAAGCATGAGGCCTTGTCTCCTTTCTATTCGGAGCGGCTGAAG 430                          440
     GluAlaHisValArgLeuTyrProSerSerArgCysThrSerGlnHisLeuLeuAsnArg
     GAGGCTCATGTCAGACTGTACCCATCCAGCCGCTGCACATCACAACATTTACTTAACAGA
```

FIG. 12-3

```
                            450                              460
        ThrValThrAspAsnMetLeuCysAlaGlyAspThrArgSerGlyGlyProGlnAlaAsn
   1321 ACAGTCACCGACAACATGCTGTGTGCTGGAGACACTCGGAGCGGCGGGCCCCAGGCAAAC 470                              480
        LeuHisAspAlaCysGlnGlyAspSerGlyGlyProLeuValCysLeuAsnAspGlyArg
        TTGCACGACGCCTGCCAGGGCGATTCGGGAGGCCCCCTGGTGTGTCTGAACGATGGCCGC 490                              500
        MetThrLeuValGlyIleIleSerTrpGlyLeuGlyCysGlyGlnLysAspValProGly
   1441 ATGACTTTGGTGGGCATCATCAGCTGGGGCCTGGGCTGTGGACAGAAGGATGTCCCGGGT 510                              520
        ValTyrThrLysValThrAsnTyrLeuAspTrpIleArgAspAsnMetArgProOP#
        GTGTACACAAAGGTTACCAACTACCTAGACTGGATTCGTGACAACATGCGACCGTGA
```

FIG. 12-4

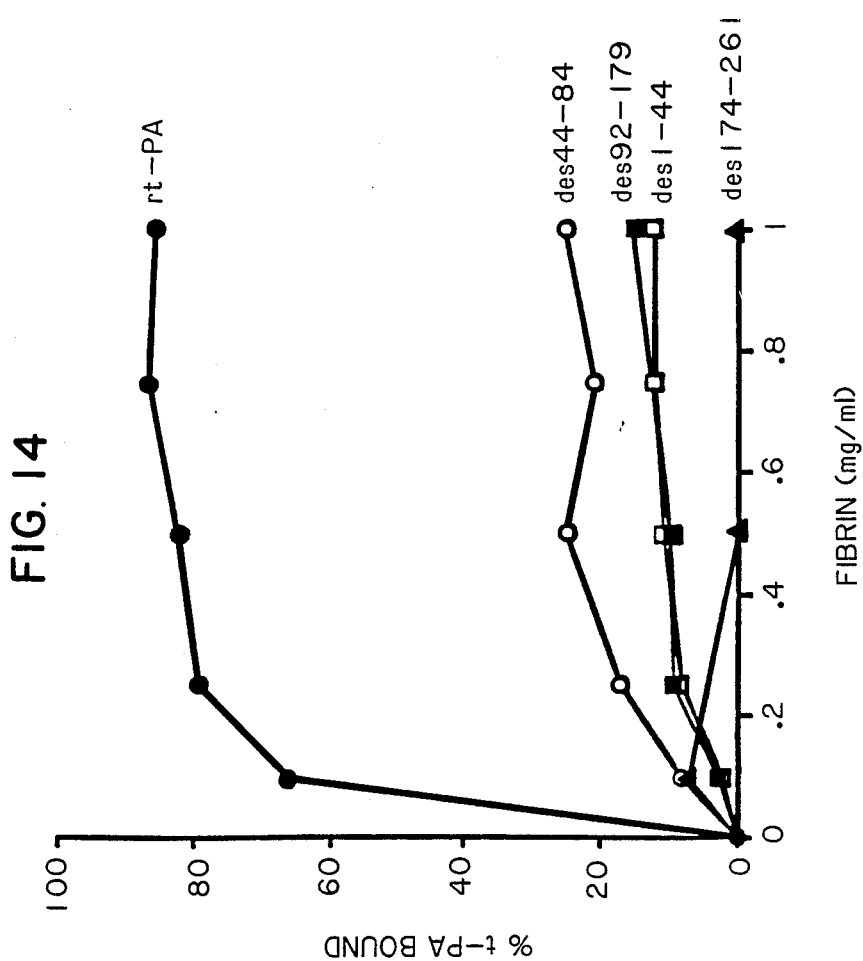

PROCESSES FOR THE PREPARATION OF T-PA MUTANTS

This is a continuing application under 35 U.S.C. 120/121 of U.S. Ser. No. 07/170,970 filed Mar. 21, 1988 now abandoned and of U.S. Ser No. 07/068,448 filed June 30, 1987 now abandoned, and the contents thereof are hereby incorporated by reference.

BACKGROUND OF THE INVENTION

1. Field of the Invention

The present invention is directed generally to processes for improving human tissue plasminogen activator (t-PA) protein and, in particular, to processes for improving the pharmacokinetic characteristics of t-PA.

2. Description of the Related Art

Human tissue plasminogen activator, t-PA, is an extremely important new biological pharmaceutical agent shown to have great promise in the treatment of vascular disease due to its high specificity and potent ability to dissolve blood clots in vivo.

Accordingly, t-PA has been hailed by medical science as one of the most impressive new agents of recent history for the treatment of vascular disease, and in particular, heart disease. For these and other reasons, t-PA will likely revolutionize the clinical management of serious vascular disease.

Human t-PA protein, as well as the underlying gene sequences which code for it, has been the subject of numerous scientific disclosures over the previous few years. For example, the structure of t-PA protein, as well as its isolation from natural sources, has been described by Rijken et al., (1981), J. Biol. Chem., 256:7035. Moreover, a patent and various patent applications have been published detailing the isolation of natural t-PA from both natural and recombinant sources (see, e.g , UK Pat. No. 2,119,804; European Patent Application Publication No. 041766; and European Patent Application Publication No. 093619) Based on such disclosures, it is now clear that natural t-PA, whether naturally isolated or a recombinant species thereof, typically includes 5 domains which have been defined with reference to homologous or similar structures identified in various other proteins. These domains have been designated as the finger (F), growth factor (G), kringle 1 (K1), kringle 2 (K2), and protease (P) regions and are situated contiguously in the N-terminus to C-terminus direction of the protein backbone structure.

In spite of the profound advantages identified with natural human t-PA as a clot dissolving pharmaceutical agent, certain drawbacks are associated with its use under various circumstances. For example natural t-PA has an extremely short plasma half-life typically about 6 minutes or so, when administered to patients in therapeutically effective amounts. Moreover, in terms of clearance rate, another important pharmacokinetic indicator, natural t-PA typically exhibits an extremely high clearance rate of about 7 to 8.5 ml/min/kg. Short half-lives and high clearance rates are desirable under certain circumstances, for example, when acute aggressive therapy of a life threatening disease such as myocardial infarction or pulmonary embolism is undertaken. In this high risk situation, patients may be treated who have significant or unrecognized potential for uncontrolled bleeding. If such bleeding would occur, drug administration could be stopped and the causative t-PA levels would be rapidly depleted by high clearance rates.

However, in other circumstances, for example, in the treatment of myocardial infarction following reperfusion, the desired therapeutic regimen is less aggressive and of extended duration (4 to 12 hours). A long half-life form of t-PA can be perceived as a more desirable, efficient and convenient treatment in patients who are not in life-threatening situations. Moreover, a longer half-life t-PA would be desirable as an agent for bolus administration, for example, by ambulance technicians, where infusion capability is generally not available, it would be much more desirable to employ t-PA-like agents having greater half-lives and/or lower clearance rates.

Accordingly, there is currently a need to identify improved processes and associated embodiments for preparing t-PA variants having improved pharmacokinetic parameters yet which retain high clot lysis activity in vivo. Such would provide medical science important new alternatives to the treatment of cardiovascular disease and in treatment of numerous other medical conditions which arise out of thromboembolic occlusion of blood vessels.

SUMMARY OF THE INVENTION

Recognizing these and other disadvantages in the art, it is a general object of the present invention to provide improved processes for the treatment of vascular disease, in particular, in the prevention of rethrombosis of coronary arteries, in affected patients.

It is a particular object of the present invention to provide processes particularly adapted for the treatment of patients in need of clot dissolving agents that have a longer half-life, and/or decreased clearance rate, relative to currently available clot dissolving agents.

It is a more particular object of the present invention to provide processes for the treatment of conditions which admit the use of clot dissolving agents having longer half-lives and/or decreased clearance rates relative to natural t-PA. for example, conditions such as deep vein thrombosis or peripheral arterial thrombosis (peripheral vascular disease).

Accordingly, in a general and overall sense, the present invention embodies a realization by the present inventors that variants of human t-PA protein may be produced which exhibit longer half-lives and/or reduced clearance rates relative to natural t-PA, yet which retain high clot lysis activity in vivo. As used herein, the term "variant human t-PA protein" refers to protein structures which include basic structural features of natural t-PA, for example, corresponding in general to amino acid sequences found in natural t-PA or to biologically functional equivalents of such sequences of amino acids, yet which structures have been altered in one or more ways to produce a variant protein having a statistically increased half-life and/or clearance rate relative to natural t-PA. As used herein, the term "natural t-PA" is meant to include t-PA, for example, as described in EPO application publications Nos. 041766 and 093619, whether obtained from natural or recombinant sources.

The present invention is thus directed generally to improved methods for the treatment of vascular disease in a patient in need of a "half-life enhanced" or "clearance rate reduced" t-PA agent. Such processes include generally preparing a variant t-PA protein which exhibits a greater plasma half-life, for example, at least about 2 times longer than that exhibited by natural t-PA, or which exhibits a reduced clearance rate, for example, about ½ or less, than the clearance rate exhibited by natural t-PA proteins. The variant t-PA protein is formulated with various pharmaceutically acceptable carriers or excipients, in amounts adequate to provide a therapeutic benefit to a patient in a convenient dosage, followed by administering appropriate amounts to a patient in need in accordance with the particular circumstances.

It will be appreciated by those of skill in the art that by "half-life" or "plasma half-life" is meant the time for a drug concentration in the plasma to be reduced by one-half, typically measured after administration of a selected dose. Accordingly, half-life measures the time of elimination of one-half the drug concentration in the plasma. In contrast, by the term "clearance rate" is meant the rate of drug elimination divided by the concentration of the drug in the particular fluid, generally plasma. By "plasma" herein is meant either plasma or serum. The concept of clearance is extremely useful in clinical pharmacokinetics because clearance of a given drug is usually constant over most clinically encountered drug concentrations, and may typically be fit to first order rate kinetics. Clearance rate may at times be more particularly defined as the dose given divided by AUC, wherein AUC is defined as the area under the plasma concentration time curve. Accordingly, by an "increased", "enhanced" or "longer" half-life is meant a half-life that is statistically longer. Moveover, by "decreased" or "reduced" clearance rate is meant one that is statistically reduced.

In that the pharmacokinetics of natural t-PA appear to be biphasic or multiphasic, such pharmacokinetics are typically fit to bi- (or multi-) exponential equations. Accordingly, it should be recognized that the half-life numbers reflected herein are "nominal" half-lives, thus reflecting the dominant half-life of natural t-PA is about 2.2 minutes for t1/2a and about 30 minutes for t1/2b. However, where Co =100, then the t1/2a component is generally about 95% and t1/2b component about 5%. Accordingly, the alpha phase is dominant and reflects the nominal half-life.

Surprisingly, it has been discovered that the key to the preparation of variant t-PA proteins which effectively retain the high in vivo clot lysis activity of natural t-PA, is the removal of all or a portion of the finger region or all or a portion of the growth factor region, or all or a portion of the Kringle 1 region, typically associated with natural t-PA. As used herein, the term "finger region" refers generally to the amino-terminus region of natural t-PA protein, which exhibits a "finger-like" structure due to the presumed location of disulfide bonds between cysteine residues 6 and 36, and 34 and 43. The finger region may be alternatively defined in terms of the underlying gene structure as the individual finger-coding exon region for example, as characterized by Type 1 homologies with fibronectin and as an independent exon region. Accordingly in certain preferred embodiments the finger region includes amino acids corresponding to amino acids about 1 (SER) through about 44 (HIS) of natural t-PA.

The growth factor region (G) has been variously defined as stretching from about amino acid 45 upwards of amino acid 91 (based upon its homology with EGF). Kringle one (K1) has been defined as stretching from about amino acid 92 to about 173 and kringle two (K2) has been defined as stretching from about amino acid 180 to about amino acid 261. The so-called serine protease domain (P) to the C-terminal end of the molecule. These domains are situated contiguously generally of one another, or are separated by short "linker" regions, and account for the entire amino acid sequence of from 1 to 527 amino acids in its putative mature form.

Each domain has been described variously as contributing certain specific activity: that is, the finger domain has been variously described as containing a sequence essential or at least of major importance for high binding affinity to fibrin. (This activity is thought important for the high specificity human tissue plasminogen activator displays with respect to clot lysis at the locus of a fibrin rich thrombus.) The growth factor-like region likewise has been associated with cell surface binding activity, at least with respect to urokinase. The Kringle 2 region has also been strongly associated with fibrin binding and with the ability of fibrin to stimulate the activity of t-PA. The serine protease domain seems to enjoy unanimous agreement of being the workhorse domain of the molecule in respect of plasminogen activating activity.

The invention therefore contemplates a process for increasing the plasma half-life of t-PA in a manner which relates to the amount or portion of finger, growth factor or Kringle 1 domain removed. Thus, the greater the degree of such domain functional alteration reflected in the t-PA variant, the greater the increase in half-life exhibited by the variant. However, it has been found that even removal of virtually the entire finger, growth factor or Kringle 1 region results in little reduction in clot lysis activity in vivo. Accordingly, pharmaceutical preparations may be readily prepared with variant t-PA proteins of the present invention which retain clot lysis activity in vivo, employing variants which include one or more of functional finger, growth factor, kringle 1, kringle 2 and/or protease domain yet having at least a portion of the finger, growth factor or Kringle 1 region removed or altered.

In certain preferred embodiments, the t-PA variants so produced and clinically employed have essentially the entire finger domain removed, characterized in particular by the removal of amino acids corresponding to amino acids 1 through 44 of natural t-PA (designated herein as "des (1-44) t-PA").

In other preferred embodiments hereof, amino acids 44 to 84, substantially the entire growth factor region, are deleted or amino acids 92 to 179, substantially the entire Kringle 1 region, are deleted.

t-PA variants prepared in accordance with the present invention exhibit plasma half-lives generally at least 2 times greater than that of natural t-PA and, in certain embodiments, exhibit half-lives between about 5 and about 20 times the plasma half-life exhibited by natural t-PA. In that the plasma half-life of natural t-PA is about 6 minutes in man, preferred variant t-PA preparations of the present invention typically exhibit half-lives of at least 12 to 20 minutes and, in the case of des (1-44) t-PA, up to an hour or more.

It will be appreciated that the "nominal" half-life of natural t-PA in rabbits, monkeys and man, are about 2, 3.5 and 6 minutes, respectively. This ratio is typically relatively constant. Thus, a half-life observed in, for example, rabbit would correspond to a somewhat greater half-life in man.

In other embodiments, the improved pharmacokinetics of variant t-PA structures is defined in terms of decreased clearance rate of the agent. In such embodiments, variant t-PA proteins are provided which exhibit clearance rates of ½ to 1/5 or less the clearance rate of natural t-PA, preferably a clearance rate of between about 1/15 and about 1/25 the clearance rate of natural t-PA. In most accepted test systems, as well as in man, natural t-PA will generally exhibit a clearance rate of on the order of 7 to 8.5 ml/min/kg. However, t-PA variants employed in the practice of the present invention will typically exhibit a clearance rate of less than about 2 ml/min/kg, with the preferred des (1–44) t-PA variant exhibiting a clearance rate of less than about 0.5 ml/min/kg.

In order to avoid the possibility of untoward effects and unknown toxicities of variant t-PA protein preparations, it is preferred although not required, that the variant protein so produced be free of synthetic derivatives, such as, for example, derivatives wherein alkyl, alkylamine or methylated benzylamines or other blocking groups are included on the protein structure.

However, other modifications have previously been found to provide improved t-PA, and such modified t-PA's may also be employed in processes of the present invention. For example novel t-PA mutant having certain amino acid substitutions in the region of amino acids 270 to about 279, and more particularly, positions 275, 276 and 277 of human t-PA have been described in U.S. Ser. No. 07/071,506, filed July 9, 1987, and its parent applications Ser. Nos. 06/846,697, filed Apr. 1, 1986 and Serial No. 06/725,468, filed April 22, 1985 all abandoned (corresponding to European Patent Application Publication No. 199,574, published Oct. 29, 1986, all of which applications are herein incorporated by reference). These mutants, characterized preferentially as t-PA mutants having an amino acid other than arginine at position 275, or lysine at position 277, are referred to herein as protease-resistant one-chain t-PA variants in that, unlike natural t-PA which can exist in both a one-chain or two-chain form, they are resistant to protease cleavage at positions 275 and/or 277 and are therefore not converted metabolically in vivo into a two-chain form. Such resistant "one-chain" variants are similarly improved by processes of the present invention and are included within the scope hereof. Examples of such enzymatically resistant (at amino acid positions 275 and/or 277) hereof include these such-like variants in combination with a missing (at least a portion of) finger, growth factor or kringle 1 region, for example des 1.44 Glu 275 t-PA and des 1–44 Glu275Iso277 t-PA.

Although it is believed that variant t-PA proteins may be obtained, for example, by enzymatic cleavage of natural t-PA followed by enzymatic addition of selected amino acids or even through totally synthetic means, in preferred embodiments t-PA variants are obtained through the practice of recombinant DNA technology and cell culture techniques. Starting recombinant vectors, and the recombinant techniques for forming, culturing and expressing appropriate t-PA variants through the use of such vectors, are known generally in the art or have been set forth in detail herein.

In general, preferred recombinant processes for preparing appropriate variant t-PA proteins includes preparing a recombinant vector which encodes the variant, for example, encoding amino acids corresponding to amino acids 45 through 527, excluding amino acids 1–44 of natural t-PA in the case of des (1–44) t-PA, aand similarly excluding the appropriate amino acids in the case of des growth factor and des kringle 1 t-PA. It will be appreciated that through the use of recombinant DNA technology to prepare variant t-PA proteins, variants are produced wherein the size and sequence of the finger, growth factor or kringle 1 region retained may be controlled with high specificity. Moreover, large quantities of variant protein may be produced and further purified by conventional means to provide pharmaceutically acceptable preparations. The product produced by genetically engineered microorganisms or cell culture systems provides an opportunity to produce human tissue plasminogen activator in a much more efficient manner than has been possible, enabling hitherto elusive commercial exploitation. In addition, depending upon the host cell, the human tissue plasminogen activator hereof may contain associated glycosylation to a greater or lesser extent compared with native material. In any event, the t-PA will be free of contaminants, such as contaminating proteins and other adventitious agents, for example, viral based entities, normally associated with it in a non-recombinant cellular environment or in pooled serum derived preparations.

The compounds of the present invention can be formulated according to known methods to prepare pharmaceutically useful compositions, whereby the modified human t-PA product of the present invention is combined in admixture with a pharmaceutically acceptable carrier vehicle. Suitable carrier vehicles and their formulation, inclusive of other human proteins, e.g., human serum albumin, are described, for example in Remington's Pharmaceutical Sciences 16th ed., 1980, Mack Publishing Co., edited by Oslo et al., which is hereby incorporated by reference. Such compositions will typically contain an effective amount of the variant t-PA, for example, from about 0.5 to about 5 mg/ml., together with a suitable amount of carrier vehicle in order to prepare pharmaceutically acceptable compositions suitable for effective administration to the host. The t-PA composition can be administered parenterally, or by other methods that ensure its delivery to the bloodstream in an effective form and amount.

Compositions particularly well suited for the clinical administration of variant t-PA products employed in the practice of the present invention include, for example, sterile aqueous solutions, or sterile hydratable powders such as lyophilized protein. It is generally desirable to further include in the formulation an appropriate amount of a pharmaceutically acceptable salt, generally in an amount sufficient to render the formulation isotonic. A pH regulator such as arginine base, and phosphoric acid, are also typically included in sufficient quantities to maintain an appropriate pH, generally from 5.5 to 7.5. Moreover to improve shelf-life or stability of aqueous formulations, it may also be desirable to further include agents such as glycerol. In this manner, variant t-PA formulations are rendered appropriate for parenteral administration, and in particular, intravenous administration.

Dosages and desired drug concentrations, of pharmaceutical compositions of the present invention may vary depending on the particular use envisioned. For example, in the treatment of deep vein thrombosis or peripheral vascular disease, "bolus" doses on the order of about 0.05 to about 0.3 mg/kg, will typically be preferred with subsequent administrations, on the order of about 0.1 to about 0.2 mg/kg, being given to maintain an approximately constant blood level, preferably on the order of about 3 $\mu$2g/ml. However, for use in connection with emergency medical care facilities where infusion capability is generally not available and due to the generally critical nature of the underlying disease (e.g., embolism, infarct), it will generally be desirable to provide somewhat larger initial doses, such as an intravenous bolus on the order of 0.3 mg/kg.

For example, the human tissue-type plasminogen activator hereof may be parenterally administered to subjects suffering from cardiovascular diseases or conditions. Dosage or dose rate may parallel that currently in use in clinical investigations of other cardiovascular, thrombolytic agents, e.g. about 1-2 mg/kg body weight as an intravenous or intra-arterial dose over 1.5-12 hours in patients suffering from myocardial infarction, pulmonary embolism, etc.

As one example of an appropriate dosage form, a vial containing 50 mg human tissue-type plasminogen activator, arginine, phosphoric acid and polysorbate 80 may be reconstituted with 50 ml sterile water for injections and mixed with a suitable volume of 0.9 percent Sodium Chloride Injection.

The extended half-life of human tissue-type plasminogen activator hereof may be suitable for rapid i.v. injection. This would eliminate the need for complex administration procedures and may increase the opportunity for the use of t-PA in settings with limited medical equipment such as in emergency vehicles staffed with paramedic personnel. An extended half-life of human tissue-type plasminogen activator may also allow lower, safer initial doses and could maintain thrombolytically effective plasma levels for up to 45 minutes or longer. A longer half-life of human tissue-type plasminogen activator may also be useful for low dose extended therapy which may be necessary to avoid reocclusion following successful acute thrombolysis or for extended thrombolysis which may be necessary in cases of peripheral vascular occlusion.

BRIEF DESCRIPTION OF THE DRAWINGS

FIGS. 1A-1C show the nucleic acid sequence, and corresponding amino acid sequence, of full-length human t-PA (amino acids 1-527), including the putative presequence region (amino acids −35 to −1), as well as 5' and 3' -flanking sequences.

FIG. 12 shows the sequence of the des 1.44 Glu 275 t-PA mutant encoded by plasmid p1154.

FIG. 14 shows the fibrin binding characteristics of the various domain deletion mutants (See FIG. 13) including finger deletions des 1-44, expressed as percent bound versus fibrin(ogen) concentration.

DETAILED DESCRIPTION OF THE PREFERRED EMBODIMENTS

I. Introduction

Figure 2:
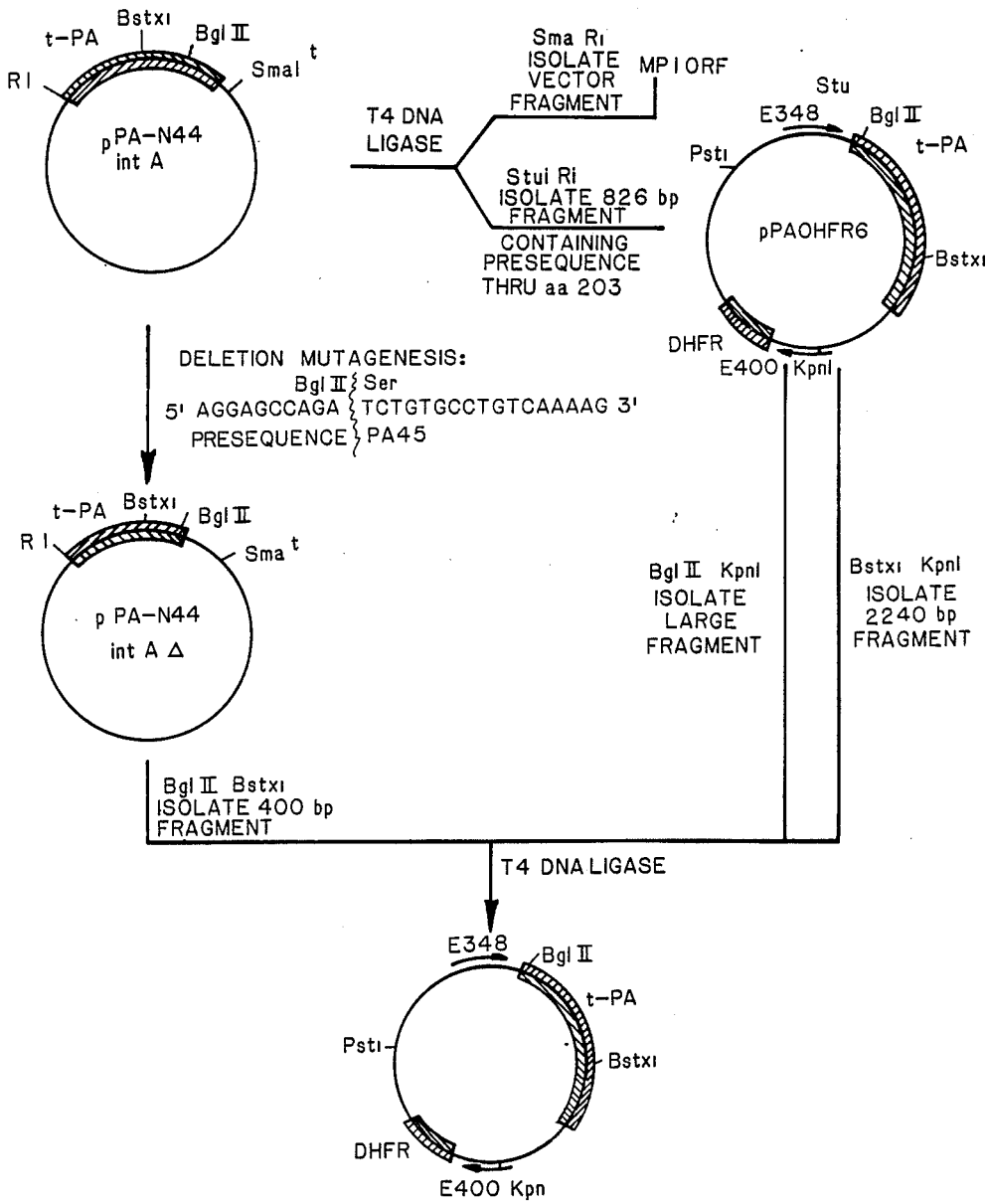
FIG. 2 shows schematically the steps taken in generating a des (1-44) t-PA variant-coding mutant plasmid.

In man and other animals, tissue-type plasminogen activator (t-PA) plays an essential role in the dissolution of fibrin clots (see, e.g., Verstraete and Collen (1986) Blood, 67:1425). t-PA is a serine protease that initiates fibrinolysis by converting plasminogen to plasmin. t-PA is composed of several domains which share sequence homology with other proteins and it has been postulated that each domain contributes a specific function to this multifunctional protein (see, e.g., Pennica et al., (1983), Nature, 301:214; Banyai et al. (1983) FEBS Lett., 163:37). Only the function of the protease domain (residues 276-527) has been unambiguously defined. This finding was first based on the observed sequence homology with other known serine proteases. More recently, limited reduction of the two-chain form of t-PA has allowed the direct isolation and functional characterization of the protease region (Rijken and Groeneveld (1986), J. Biol. Chem., 261:3098; Dodd et al. (1986), Thrombos. Haemostas., 55:94).

However, the precise function(s) of the finger domain (e.g.. see FIGS. 1 A-C; residues 1-44 which are homologous with the type 1 finger regions of fibronectin), the growth factor domain (residues 45-89, which are homologous to epidermal growth factor, and the growth factor regions in urokinase, factor IX, factor X and protein C) and the two kringle domains (residues 92-173, and 180-261, which are homologous to the kringle regions in plasminogen, prothrombin, urokinase, and factor XII) are presently unknown. Banyai, et al., supra, employed sequence homology with the finger domains responsible for the fibrin affinity of fibronectin and limited proteolytic studies on t-PA to suggest that the amino-terminal finger domain is responsible for t-PA's fibrin affinity. Alternatively, Ichinoise, et al. (1986), J. Clin. Invest., 78:103, have used sequence homology with the kringle domains responsible for the fibrin affinity of plasminogen and limited proteolysis to suggest that the second kringle domain of t-PA is responsible for the interaction with fibrin.

Site-specific mutagenesis is a technique which allows for the selective deletion of desired portions of a particular protein through selective deletion of corresponding underlying gene sequences. When combined with functional characterization of the resulting mutant, such techniques may allow elucidation of the function or functions of each domain. For example, Bang, et al. (1985), Clin. Res., 33:878A have presented preliminary work using this approach, which indicates that the finger and growth factor domains are sufficient for fibrin binding and maximal stimulation of the activity by fibrin. In contrast, van Zonneveld, et al. (1986), Proc. Natl. Acad. Sci. U.S.A., 83:4670, have shown by using a transient expression system and unpurified supernatants that the second kringle domain and to a lesser extent the finger and growth factor domains are responsible for fibrin binding. However, Kagitani, et al. (1985), FEBS Lett., 189:145, isolated a naturally occurring t-PA cDNA coding for residues 50-527 from Detroit 562 cells and characterized the protein after expression in *E. coli*. In contrast to other researchers, they found that this mutant which was missing the finger domain and a portion of the growth factor domain did bind to fibrin.

Verheijen et al., *EMBO* 5, 3525 (1986) have prepared a series of variants of t-PA lacking one or more domains. They found that in the absence of plasminogen at low concentrations of fibrin, removal of the finger domain significantly decreased fibrin binding; however, at high concentrations of fibrin, the presence of the second kringle domain seems sufficient to ensure significant binding. In the presence of plasminogen, the kringle two domain is also important at low fibrin concentrations. They also concluded that only the kringle two domain is involved in stimulation of activity by fibrin.

Accordingly, there has been much confusion and uncertainty surrounding the functional significance of the various structural domains, and in particular, the role played by the N-terminal finger domain of natural t-PA. However, based upon the present invention, it can now be unequivocally disclosed that among certain other possible pharmacologic attributes of the finger, growth factor or kringle 1 domain, it is clear that the presence of these domains in t-PA proteins directly correlates with the short half-life of natural t-PA. In particular, it can now be disclosed that removal of the finger, growth factor or kringle 1 region, for example, as exemplified by removal of the first 44 amino acids of natural t-PA in the case of removal of the finger region, results in a variant t-PA proteins that exhibit surprising and unexpected pharmacokinetic properties in light of what has previously been known regarding natural t-PA and its associated intramolecular structures.

II. Preparation of t-PA Variants

As noted above, recombinant techniques are preferred for the preparation of t-PA variants employed in the processes of the present invention. In particular, recombinant DNA technology is employed for the preparation of these human t-PA deletion mutants, variously modified by resultant single or multiple amino acid substitutions, deletions, additions and replacements, for example, by means of site directed deletion mutagenesis. Included would be the preparation of t-PA deletion variants having all or part of the finger region deleted, yet retaining the kringle region(s) and serine protease region characteristic generally of human tissue plasminogen activator described previously (e.g., see UK Patent No. 2,119,804, incorporated herein by reference). but otherwise modified by removal or alteration of the finger region.

It will be appreciated by those of skill in the art that, in the context of the specific deletions employed in the practice of the instant processes, as used herein, "human tissue plasminogen activator", "human t-PA" or "natural t-PA" denotes human extrinsic (tissue-type) plasminogen activator, produced by microbial or cell cultures systems, in bioactive forms comprising a protease portion and corresponding to those tissue plasminogen activators otherwise native to human tissue. The human tissue plasminogen activator protein produced herein has been defined by means of determined DNA gene and deductive amino acid sequencing (see FIGS. 1 A-C). It will be understood that natural allelic variations exist and occur from individual to individual. These variations may be demonstrated by amino acid differences in the overall sequence or by deletions, substitutions, insertions, inversions or additions of amino acids in said sequence. In addition, the location of and degree of glycosylation depend on the nature of the host cellular environment.

All such allelic variations and modifications resulting in derivatives of human tissue plasminogen activator characterized as biological functional equivalents of t-PA are included within the scope of this invention, as well as other related human extrinsic (tissue-type) plasminogen activators, similar physically and biologically, so long as the essential, characteristic human tissue plasminogen activator activity remains unaffected in kind. Moreover, it is known that certain alterations may be made in the amino acid sequence without altering the underlying biological function of the protein. For example, it is known that amino acids may be exchanged with various other amino acids based on a correlation of the hydropathic index of the two exchanged amino acids.

As with t-PA, variant t-PA of the present invention is typically prepared (1) having methionine as its first amino acid (present by virtue of the ATG start signal codon insertion in front of the structural gene) or (2) where the methionine is intra- or extracellularly cleaved, having its normally first amino acid, or (3) together with either its signal polypeptide or a conjugated protein other than the conventional signal polypeptide, the signal polypeptide or conjugate being specifically cleavable in an intra-or extracellular environment, or (4) by direct expression in mature form without the necessity of cleaving away any extraneous, superfluous polypeptide. The latter is particularly important where a given host may not, or not efficiently, remove a signal peptide where the expression vehicle is designed to express the tissue plasminogen activator together with its signal peptide. In any event, the thus produced human variant t-PA, in its various forms, is recovered and purified to a level fitting it for use in the treatment of the various vascular conditions or diseases.

Furthermore, t-PA has forms which include both the single chain (non-protease resistant 1-chain) protein and the 2-chain protein. The latter is proteolytically derived from the nonresistant 1-chain compound. It is theorized that the 2-chain occurs at the locus of the conversion of plasminogen to plasmin. The present invention provides for the administration of variant 1-chain protein, whether protease resistant or not, or for the administration of 2-chain protein, which has also been shown to be active. The 2-chain protein can be prepared by in vitro proteolytic conversion after the nonresistant 1-chain material is produced. A so-called "kringle" area is positioned upstream from the serine protease portion and is believed to play an important function in binding the tissue plasminogen activator hereof to a fibrin matrix, hence, the observed specific activity of the present tissue plasminogen activator toward tangible, extant thrombi. The tissue plasminogen activator hereof is produced containing the enzymatically active portion corresponding to native material and the term human tissue plasminogen activator defines products comprising such portion alone or together with additional amino acid sequences up to the full length molecule.

"Essentially pure form" when used to describe the state of the variant human t-PA produced by the invention means free of protein or other materials normally associated with human t-PA when produced by non-recombinant cells, i.e. in its "native" environment.

"DHFR protein" refers to a protein which is capable of the activity associated with dihydrofolate reductase (DHFR) and which, therefore, is required to be produced by cells which are capable of survival on medium deficient in hypoxanthine, glycine, and thymidine (−HGT medium). In general, cells lacking DHFR protein are incapable of growing on this medium, cells which contain DHFR protein are successful in doing so. For this reason, inclusion of DHFR-coding sequences in recombinant vectors of the present invention allows a means of selecting successfully transformed hosts.

"Cells sensitive to MTX" refers to cells which are incapable of growing on media which contain the DHFR inhibitor methotrexate (MTX). Thus, "cells sensitive to MTX" are cells which, unless genetically altered or otherwise supplemented, will fail to grow under ambient and medium conditions suitable for the cell type when the MTX concentration is 0.2 ug/ml or more. Some cells, such as bacteria, fail to exhibit MTX sensitivity due to their failure to permit MTX inside their cell boundaries, even though they contain DHFR which would otherwise be sensitive to this drug. Thus, in general, cells which contain DHFR will be sensitive to methotrexate only if they are permeable to, or capable of uptake of, MTX.

"Wild type DHFR" refers to dihydrofolate reductase as is ordinarily found in the particular organism in question. Wild type DHFR is generally sensitive in vitro to low concentrations of methotrexate.

"Expression vector" includes vectors which are capable of expressing DNA sequences contained therein, where such sequences are operably linked to other sequences capable of effecting their expression. It is implied, although not always explicitly stated, that these expression vectors must be replicable in the host organisms either as episomes or as an integral part of the chromosomal DNA. Clearly a lack of replicability would render them effectively inoperable. In sum, "expression vector" is given a functional definition, and any DNA sequence which is capable of effecting expression of a specified DNA code disposed therein is included in this term as it is applied to the specified sequence. In general, expression vectors of utility in recombinant DNA techniques are often in the form of "plasmids" which refer to circular double stranded DNA loops which in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Recombinant host cells" refers to cells which have been transformed with vectors constructed using recombinant DNA techniques. As defined herein, variant t-PA is produced in the amounts achieved by virtue of this transformation, rather than in such lesser amounts, or, more commonly, in such less than detectable amounts, as might be produced by the untransformed host. t-PA produced by such cells can be referred to as "recombinant t-PA".

As used herein, a "biological functional equivalent" of t-PA or variant t-PA, refers to natural or variant t-PA wherein the natural sequence (or corresponding variant sequence). for example, as illustrated in FIGS. 1A–1C, is replaced by one having a similar biological function. For example, it has been found by Kyte et al. (1982). J. Mol. Biol., 157:105, that certain amino acids may be substituted for other amino acids having a similar hydro-pathic index or score, and still retain a similar biologic activity. As displayed in the table below, amino acids are assigned a hydropathic index on the basis of their hydrophobicity and charge characteristics. It is believed that the relative hydropathic character of the amino acid determines the secondary structure of the resultant protein, which in turn defines the interaction of the protein with its receptor In the case of t-PA, it is believed that biological functional equivalents of t-PA may be obtained by substitution of amino acids having similar hydropathic values. As used herein, a biological functional equivalent of t-PA or variant t-PA in terms of biological activity. Thus, for example, isoleucine, which has a hydropathic index of 4.5, can be substituted for valine (+4.2) or leucine (+3.8), and still obtain a protein having like biological activity. Alternately, at the other end of the scale, lysine (−3.9) can be substituted for arginine (+4.5), and so on. In general, it is believed that amino acids can be successfully substituted where such amino acid has a hydropathic score of within about +/−1 hydropathic index unit of the replaced amino acid.

| Amino Acid | Hydropathic Index |
|---|---|
| Isoleucine | 4.5 |
| Valine | 4.2 |
| Leucine | 3.8 |
| Phenylalanine | 2.8 |
| Cysteine/cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 | a. Site-Specific Deletion Mutazenesis

As discussed above, TPA variants hereof are preferably produced by means of specific deletion mutations. Deletion mutants useful in the practice of the invention are formed most readily through the use of specific oligonucleotide sequences which encode the DNA sequence of the desired deletion junction, as well as a sufficient number of adjacent nucleotides, to provide a primer sequence of sufficient size and sequence complexity to form a stable duplex on both sides of the deletion junction being traversed. Typically, a primer of at least 27 nucleotides in length is preferred, with about 10 nucleotides on the 5' side of the junction and 17 on the 3' side.

Accordingly, for the preparation of the preferred des (1-44) t-PA variant a primer having the sequence:

is preferably employed. However, it will be apparent that any degree of finger deletion can be accomplished through the use of similar DNA primers. Thus, for example, for deletion mutants encoding increasing carboxy and/or amino terminal portions of the finger region, one would substitute the above primer with one having the sequence:

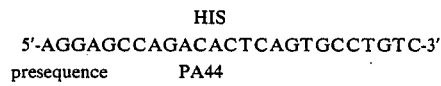

and so on. Thus, by "walking" the finger region deletion from a total deletion (e.g., des 1-44) to decreasing deletions (e.g., des 1-43, des 2-43, des 2-42, and so on), variant t-PA's are provided of varying improved pharmacokinetic parameters relative to natural t-PA. The particular methodology, reagents, etc., which may be employed to prepare various such deletion variants is disclosed below in connection with examples demonstrating the development of CVSVPA-N44 (D22), a plasmid encoding des (1-44) t-PA, or involves techniques known in the art.

Accordingly, appropriate deletion variants of the t-PA gene may be prepared in this general fashion from known t-PA encoding vectors, which deletion mutants may then be further employed to transform appropriate hosts.

b. Host Cell Cultures and Vectors

The vectors and method disclosed herein are suitable for use in host cells over a wide range of prokaryotic and eukaryotic organisms.

In general, or course, prokaryotes are preferred for cloning of DNA sequences in constructing the vectors useful in the invention. For example, *E. coli* K12 strain 294 (ATCC No. 31446) is particularly useful. Other microbial strains which may be used include *E. coli* strains such as *E. coli* B, and *E. coli* X1776 (ATTC No. 31537). These examples are, of course, intended to be illustrative rather than limiting.

Prokaryotes may also be used for expression. The aforementioned strains, as well as *E. coli* W3110 (F−, λ−, prototrophic, ATTC No. 273325), bacilli such as *Bacillus subtilus,* and other enterobacteriaceae such as *Salmonella typhimurium* or *Serratia marcesans,* and various pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR 322, a plasmid derived from an *E. coli* species (see, e.g., Bolivar, et al., Gene 2: 95 (1977)). pBR 322 contains genes for ampicillin and tetracycline resistance and thus provides easy means for identifying transformed cells. The pBR 322 plasmid, or other microbial plasmid or phage must also contain, or be modified to contain, promoters which can be used by the microbial organism for expression of its own proteins.

Those promoters most commonly used in recombinant DNA construction include the B-lactase (penicillinase) and lactose promoter systems (Chang et al., Nature, 375: 615 (1978); Itakura, et al., Science, 198: 1056 (1977); Goeddel, et al. Nature 281: 544 (1979)) and a tryptophan (trp) promoter system Goeddel, et al., Nucleic Acids Res., 8: 4057 (1980); EPO Appl Publ No. 0036776). While these are the most commonly used, other microbial promoters have been discovered and utilized, and details concerning their nucleotide sequences have been published, enabling a skilled worker to ligate them functionally with plasmid vectors (see, e.g., Siebwenlist, et al. Cell 20: 269 (1980)).

In addition to prokaryotes, eukaryotic microbes, such as yeast cultures may also be used. *Saccharomyces cerevisiase,* or common baker's yeast is the most commonly used among eukaryotic microorganisms, although a number of other strains are commonly available. For expression in Saccharomyces, the plasmid YRp7, for example, (Stinchcomb, et al., Nature, 282: 39 (1979); Kingsman et al., Gene, 7: 141 (1979); Tschemper, et al.. Gene, 10: 157 (1980)) is commonly used. This plasmid already contains the trpl gene which provides a selection marker for a mutant strain of yeast lacking the ability to grow in tryptophan, for example ATCC No. 44076 or PEP4-1 (Jones, Genetics, 85: 12 (1977)). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman, et al., J. Biol. Chem., 255: 2073 (1980)) or other glycolytic enzymes (Hess, et al., J. Adv. Enzyme Reg., 7: 149 (1968); Holland, et al., Biochemistry, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase. phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [Tissue Culture, Academic Press, Kruse and Patterson. editors (1973)]. Examples of such useful host cell lines are VERO and HeLa cells, Chinese hamster ovary (CHO) cell lines, and W138, BHK, COS-7 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., Nature, 273: 113 (1978). Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g. Polyoma, Adeno, VSV, BPV) source, or may be provided by the host cell chromosomal replication mechanism. If the vector is integrated into the host cell chromosome, the latter is often sufficient.

In selecting a preferred host cell for transfection by the vectors of the invention which comprise DNA sequences encoding both variant t-PA and DHFR protein, it is appropriate to select the host according to the type of DHFR protein employed. If wild type DHFR protein is employed, it is preferable to select a host cell which is deficient in DHFR, thus permitting the use of the DHFR coding sequence as a marker for successful transfection in selective medium which lacks hypoxanthine, glycine, and thymidine. An appropriate host cell in this case is the Chinese hamster ovary (CHO) cell line deficient in DHFR activity, prepared and propagated as described by Urlaub and Chasin, Proc. Natl. Acad. Sci. (U.S.A.) 77: 4216 (1980).

On the other hand, if DHFR protein with low binding affinity for MTX is used as the controlling sequence it is not necessary to use DHFR deficient cells. Because the mutant DHFR is resistant to methotrexate, MTX containing media can be used as a means of selection provided that the host cells are themselves methotrexate sensitive. Most eukaryotic cells which are capable of absorbing MTX appear to be methotrexate sensitive. One such useful cell line is a CHO line, CHO-K1 ATCC No. CCL 61.

Satisfactory amounts of human t-PA are produced by cell cultures, however, refinements using a secondary coding sequence serve to enhance production levels even further. The secondary coding sequence comprises dihydrofolate reductase (DHFR) which is affected by an externally controlled parameter, such as methotrexate, thus permitting control of expression by control of the methotrexate (MTX) concentration.

c. Methods Employed

If cells without formidable cell membrane barriers are used as host cells, transfection is carried out by the calcium phosphate precipitation method as described by Graham and Van der Eb, Virology, 52: 546 (1978). However, other methods for introducing DNA into cells such as by nuclear injection or by protoplast fusion may also be used.

If prokaryotic cells or cells which contain substantial cell wall constructions are used, the preferred method of transfection is calcium treatment using calcium chloride as described by Cohen, F. N. et al., Proc. Natl. Acad. Sci. (U.S.A.) 69: 2110 (1972).

Construction of suitable vectors containing the desired coding and control sequences employ standard ligation techniques. Isolated plasmids or DNA fragments are cleaved, tailored, and relegated in the form desired to form the plasmids required.

Cleavage is performed by treating with restriction enzyme (or enzymes) in suitable buffer. In general, about 1 ug plasmid or DNA fragments is used with about 1 unit of enzyme in about 20 ul of buffer solution. (Appropriate buffers and substrate amounts for particular restriction enzymes are specified by the manufacturer.) Incubation times of about 1 hour at 37' are workable. After incubations, protein is removed by extraction with phenol and chloroform, and the nucleic acid is recovered from the aqueous fraction by precipitation with ethanol.

If blunt ends are required, the preparation is treated for 15 minutes at 15° C. with 10 units of Polymerase I (Klenow), phenol-chloroform extracted, and ethanol precipitated.

Size separation of the cleaved fragments is performed using 6 percent polyacrylamide gel described by Goeddel, D., et al., Nuclei Acids Res., 8: 4057 (1980).

For ligation approximately equimolar amounts of the desired components, suitably end tailored to provide correct matching are treated with about 10 units T4 DNA ligase per 0.5 ug DNA. (When cleaved vectors are used as components, it may be useful to prevent religation of the cleaved vector by pretreatment with bacterial alkaline phosphatase.)

As discussed above, t-PA variants hereof are preferably produced by means of specific deletion mutation. Deletion mutants useful in the practice of the present invention are formed most readily through the use of specific oligonucleotide sequences which encode the DNA sequence of the desired deletion junctions, as well as a sufficient number of adjacent nucleotides, to provide a sequence of sufficient size and sequence complexity to form a stable duplex on both sides of the deletion junction being traversed.

For analysis to confirm correct sequences in plasmids constructed, the ligation mixtures are used to transform E. coli K 12 strain 294 (ATCC 31446) and successful transformants selected by ampicillin or tetracycline resistance where appropriate. Plasmids from the transformants are prepared, analyzed by restriction and/or sequenced by the method of Messing et al., Nucleic Acids Res., 9:309 (1981) or by the method of Maxam et al., Methods of Enzymology, 65:499 (1980).

Amplification of DHFR protein coding sequences is effected by growing host cell cultures in the presence of approximately 20–500,000 nM concentrations of methotrexate, a competitive inhibitor of DHFR activity. The effective range of concentration is highly dependent, of course, upon the nature of the DHFR gene, protein and the characteristics of the host. Clearly, generally defined upper and lower limits cannot be ascertained. Suitable concentrations of other folic acid analogs or other compounds which inhibit DHFR could also be used. MTX itself is, however, convenient, readily available and effective.

In the examples which follow, preferred embodiments are disclosed in the form of experiments conducted by applicants to demonstrate the practice and surprising utility of the present invention. It will be appreciated by those of skill that these methods represent those found by the present inventors to work well in the practice of the invention and as such, these experiments in no way represent the only means to achieve the advantages of the invention.

EXAMPLE I

Preparation of des (1–44) Human t-PA Variant

As discussed briefly above, the most convenient method for introducing specific deletions in the finger region of natural t-PA is through site-specific deletion mutagenesis of the underlying cDNA gene sequences. This method employs a single-stranded synthetic "primer" sequence that encodes the desired new sequence. The new primer is hybridized to a single-stranded template bearing complementary sequences, typically a template encoding the gene from which sequences are to be deleted. After the primer is extended through the use of a DNA polymerase, the hybrid molecule is allowed to replicate in a suitable host.

To prepare a des (1–44) t-PA mutant, site-directed deletion mutagenesis was practiced using a starting plasmid which encodes the t-PA cDNA structural gene and a part of the 3' untranslated region. The preparation of this plasmid, pPADHFR-6 (also designated pETPFR), as well as conditions for its expression in suitable hosts and purification of the resultant protein, is described in detail in EPO Application Publication No. 093,619, incorporated herein by reference. A schematic diagram of the steps taken in performing the deletion is shown in FIG. 2. The basic methodology employed is disclosed in Adelman, et al. (1983), DNA, 2:183, incorporated herein by reference.

Plasmid pPADHFR.6 was digested with StuI and EcoRI to release an 826 base pair fragment which included sequences encoding the t-PA presequence through amino acid 203. This fragment was ligated with the vector fragment of SmaI/EcoRI digested M13mp10RF, a replicative form M13 phage vector (see, e.g., Messing, et al. Third Cleveland Symposium on Macromolecules Recombinant DNA, Editor A. Walton, Elsevier, Amsterdam (1981)). The intermediate plasmid, pPA-N44intA, was thus a replicative form of M13 phage which included the portion of the t-PA gene from which the codons for amino acids 1–44 were to be removed by site-directed deletion mutagenesis.

To perform the mutagenesis, an oligonucleotide primer was prepared by a method such as the phosphotriester method of Crea, et al., (1978) Proc. Natl. Acad. Sci. U.S.A., 75:5765. The primer employed to prepare a des (1–44) mutant was as follows:

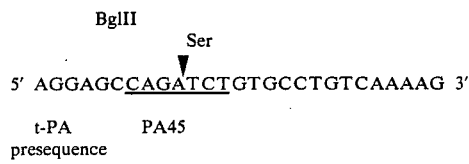

```
         BglII
          Ser
           ↓
5' AGGAGCCAGATCTGTGCCTGTCAAAAG 3' t-PA        PA45
presequence
```

As will be appreciated, the ten 5' nucleotides of this primer encode presequence amino acids −3 to −1 (gly-ala-arg), whereas the seventeen 3' nucleotides encode amino acids 45 through 49 (SER-VAL-PRO-VAL-LYS). Note that the "TCT" codon was employed for serine-45 in order to retain the BglII site.

Approximately 200 mg of the synthetic oligonucleotide was phosphorylated for 30 minutes at 37° C. in 30 ul of 50 mM-Tris-HCl, pH 7.5, 10 mM MgCl2, 10 mM dithiothreitol, 1 mM ATP containing about 8 U of T4 polynucleotide kinase. For heteroduplex formation about 50 ng single-stranded pPA-N44intA was heated to 95° C. (10 min), and slowly cooled to room temperature (30 min), then to 4° C., in about 40 ul 10 mM Tris-HCl, pH 7.5, 10 mM MgCl2, 1 mM dithiothreitol containing 100 ng of the phosphorylated primer. Primer extension was started by the addition of 10 ul ligase buffer containing 2 mM ATP, 0.25 mM each of dGTP, dCTP, dATP, dTTP, 5 U of E. coli polymerase I large (Klenow) fragment and 400 U of T4 DNA ligase. After 1 hour at 15° C. the reaction mixture was used to transform JM101 cells.

Transformation was performed by mixing all of the ligation mixture with 200 ul of competent JM101 cells, followed by incubation on ice for 30' and 5' at 37° C. Then 3.5 ml. 2YT top agar at 55' was mixed with 200 ul. of the phage-saturated cells, 10 ul IPTG (200 mM) and 50 ul X gal and after addition, the cells were plated onto Petri dishes containing 2YT with no drugs.

Colorless plaques were picked and transferred to a microtiter dish containing 100 ul 2YT medium. The inoculated microtiter fluids were stamped on 15 cm diameter LB agar plates overlayed with a lawn of 600 ul JM101 cells in 8 ml 2YT top agar and incubated overnight at 37° C. The formed plaques were transferred to a nitrocellulose disc by physical contact for 1 min. The nitrocellulose disc was treated with 0.5M NaOH, 1.5M NaCl for 3 min and washed twice with 3M NaCl.0.5M Tris HCl pH 7.5 for 15 min and then with 2X SSC for 15 min. Prehybridization mix contains 10 mM Tris pH 7.5, 5 mM EDTA. 0.9M NaCl, 1X Denhardt 0.5 percent NP40, 100 uM ATP. 1 mM sodium pyrophosphate, 1 mM sodium phosphate and 50 ug/ml E. coli tRNA. 1X Denhardt's contains per liter 200 mg Ficoll, 200 mg polyvinylpyrrolidone, 200 mg bovine serum albumin (BSA., fraction V). The disc was baked at 80° C. in vacuo for 90 min. The disc was then incubated for 3 hrs with 6 ml prehybridization fluid in a Petri dish followed by addition of 5×106 cpm labeled primer and hybridized overnight. Selective washing of the disc was performed with 0.4X SSC at 49° C. and after air-drying the disc was exposed to X-ray film. Positively hybridizing clones were further analyzed by dideoxy sequencing. See Adelman, Ibid. From the positive colonies, a recombinant plasmid, designated pPA-N44intA delta, was selected which contained the proper deletion.

In order to replace the mutant gene sequence from the M13 phage into proper expression context into the DHFR-containing expression vector, plasmid pPADHFR6 was digested separately with BglII/KpnI, to isolate the large fragment encoding the DHFR gene, and BstXI/KpnI, to isolate a 2240 base fragment encoding the 3' end (amino acids 45–527) of natural t-PA. A 400 base fragment bearing the N44 mutation was isolated from pPA-N44intA delta by digestion with BglII/BstXI, and ligated together with the two fragments derived from pPADHFR6. The product of this ligation, designated CVSVPA-N44 D22, was thus a copy of the parental plasmid pPADHFR6, except having codons encoding amino acids 1–44 removed.

EXAMPLE I

Transfection of CHO Cells with CVSVPA-N44 (D22)

The recombinant plasmid CVSVPA-N44 (D22) was expressed in DHFR-CHO cells, prepared as discussed above. The CHO cells were grown to approximately 75% confluency, and transfected with approximately 2 ug plasmid DNA (about ½ normal miniscreen) which had previously been subjected to RNase in Tris-EDTA buffer. The DNA was brought to 50 mM CaPO$_4$/-HEPES and this material was employed to transfect the cells generally by the method of Graham et al. (1978), Virology, 52:546. Briefly, the media was removed from the monolayer cells in a 100 mm culture dish, and replaced with about 5 ml of Ham's F12 media with 10% FCS. The calcium-precipitated DNA was put on the cells and allowed to sit at 37° C. for two hours.

After about 2 hours, the cells were glycerol-shocked by removing the old media and adding 1 ml shock solution (20% glycerol in PBS) for about 45 seconds. The cells were then washed with F12 media to remove glycerol and refed with fresh media for about 48 hours. At this point, the cells were split about 1/10 and replaced on selective media (Ham's F12, G- H- T-, with 10% extensively dialyzed FCS). After plating on selective media, the cells were frozen until used for preparation of Des (1-44) t-PA.

EXAMPLE III

Preparation of des (1-44) Human t-PA

Des 1-44 t-PA was expressed in Chinese hamster ovary (CHO) cells as discussed above. The supernatants were collected, filtered, and stored at −20° C. in the presence of aprotinin. The t-PA was purified from cell supernatants using published procedures (see, e.g. UK patent No. 2, 119,804; EPO application publication Nos. 041,766, 093,619 or 0,199,574, all incorporated herein by reference) or a monoclonal antibody column. In particular, transformed CHO cells were grown to confluency in roller bottles in F12 medium containing 10% FBS, 500 mM MTX, 200 mM glutamine, 20 mM Hepes, 100 U/ml pen-strep, after which time the media was replaced with serum-free medium, and incubation continued for 5.6 days. The cells were separated and the supernatant passed over a Zn-chelating column (see, e.g. EPO publication No. 0,199,574) and washed with 2 column volumes of 1M NaCl, 50 nM Tris, pH 8.0. The t-PA variant was then eluted with same buffer including 50 mM imidazole, and tubes bearing activity pooled.

This material was then dialyzed into 25 mM Tris, 0.5M NaCl, pH 8.0, and passed over a lysine-sepharose column. Following washing with 2 column volumes of 0.8M NaCl, 40 mM NaPO$_4$, it was eluted with 50 mM NaPO$_4$, 0.2M arginine, pH 7.2-7.4. Although the concentration of arginine required to elute des 1-44 t-PA from lysine-agarose was similar to the concentration required to elute normal sequence t-PA, it was necessary to load the column very slowly with des 1-44 t-PA to ensure that it would bind.

Protein concentrations were determined by an ELISA, and standardized to amino acid analysis of both des 1-44 t-PA and normal sequence t-PA. Protein purity and homogeneity were analyzed by N-terminal sequencing on a prototype gas/liquid phase sequencer, and by polyacrylamide gel electrophoresis in the presence of sodium dodecyl sulfate (PAGE-SDS) with the buffer system of Laemmli (1970) Nature, 227:680. Typically 7 to 17% gradient gels were used and proteins were visualized with the silver-stain technique of Morrissey (1981), Anal. Biochem., 117:307. Natural sequence t-PA was expressed and purified in a similar manner.

Figure 3:
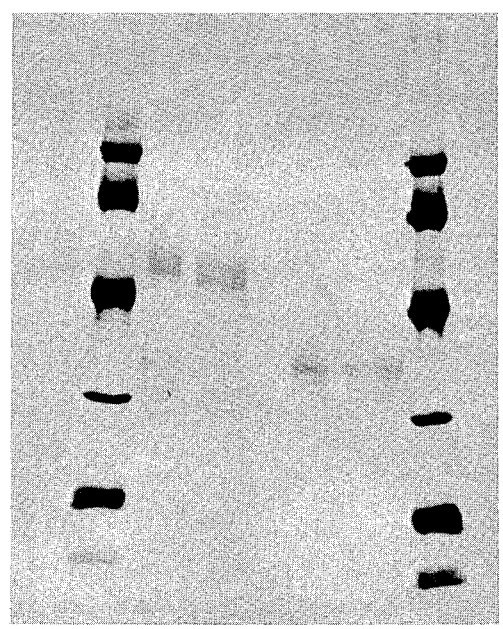
FIG. 3 shows a polyacrylamide gel comparing the migration of natural t-PA to the des (1-44) variant t-PA, both in the presence and absence of reducing agents.

Both t-PA and des 1-44 t-PA were purified to homogeneity using identical techniques and each protein exhibited the expected molecular weight on SDS-PAGE. Although synthesized as one polypeptide chain, nonresistant one-chain t-PA can be readily hydrolyzed at the Arg275-Ile276 peptide bond to yield a two-chain form. FIG. 3 shows that in the absence of reducing agents, the apparent Mr's of t-PA and des 1-44 t-PA are approximately 60,000 and 55,000, respectively. When the two-chain forms of the proteins were reduced by the addition of dithiothreitol, t-PA exhibited bands at about 35,000 daltons and a diffuse band from about 30,000 to 34,000 daltons, corresponding to the protease portion of the molecule (residues 275-527), and the amino-terminal finger, growth factor and kringle domains (residues 1-275), respectively. Des 1-44 t-PA exhibited bands at Mr's of about 35,000 and a diffuse band from about 25,000 to 30,000 which corresponds to a protease portion identical to that in t-PA and an amino-terminal domain at a lower molecular weight than the corresponding domain in t-PA. The identification of these bands was confirmed by a western blot using antibodies to the amino-terminal half of t-PA.

Amino-terminal sequencing of samples of both proteins showed that each protein had a minor sequence I-K-G corresponding to residues 276-278, indicating that the samples were in the two-chain form. The other major sequence in the t-PA sample was S-Y-Q, corresponding to residues 1-3. In des 1-44 t-PA the major sequence was S-V-P, which corresponds to residues 45-47 and confirms that the finger domain (residues 1-44) was deleted and that the mutant protein was expressed and processed properly with residue 45 as the new amino terminal.

Figure 4:
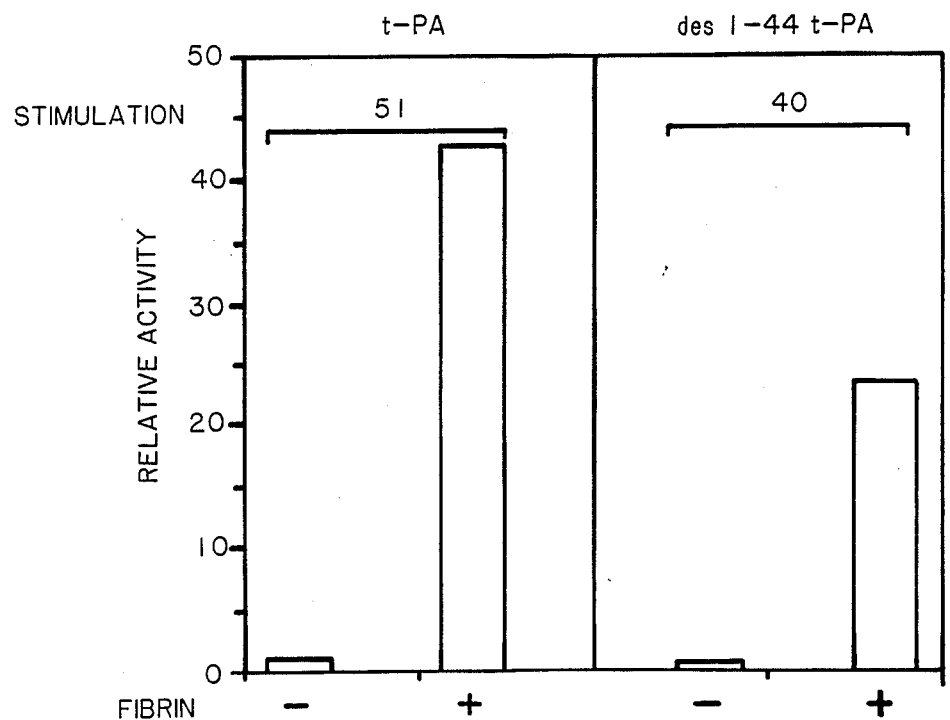
FIG. 4 compares the fibrin stimulation of des (1-44) t-PA and natural t-PA in vitro using the plasmin specific substrate S-2251.

Although the results of SDS-PAGE and sequence analysis verified that des 1-44 t-PA was a homogeneous protein with the expected molecular weight and sequence, deletion of one domain of the protein may have significant effects on the structure and folding of the rest of the molecule. Although no direct tests are available to examine the secondary and tertiary structure on the molecule, we have determined that limited proteolysis is effective in identifying improperly folded molecules. When the degradation pattern of trypsin-treated t-PA and des 1-44 t-PA were compared no differences were observed (FIG. 4). Although the amino-terminal domain in the des 1-44 t-PA samples (see FIG. 4) has a lower molecular weight than the corresponding domain in t-PA, neither the protease nor the amino-terminal domain of des 1-44 t-PA was more susceptible to proteolysis by trypsin. Proteolysis at higher trypsin t-PA ratios and several ratios of chymotrypsin and pepsin to t-PA also showed no differences in the rate of proteolysis.

EXAMPLE IV

Preparation and Utilization of Expression Vector for Recombinant Production of des 1-44 GLU 275 t-PA Variants Hereof 1. Plasmid Constructions
a. Plasmid p1154
(1) Plasmid pPADHFR-6

Plasmid pPADHFR-6 (otherwise referred to as pETPFR) was prepared as described, for example, in European Patent Application Publication No. 93619, supra, which is hereby incorporated by reference. See FIG. 1 for perspective details. Superfluously, this plasmid, per se and in transfected form in CHO cells, has been deposited on 15 Dec. 1987 with the American Type Culture Collection, Rockville, Md., U.S.A. under ATCC Nos. 40403 and CRL 9606, respectively.

(2) Plasmid pCVSVPA-N44 D22

Plasmid pCVSVPA-N44 D22 was prepared as described above. To recapitulate, plasmid pPADHFR-6 (supra) was digested with StuI and EcoRI to release an 826 base pair fragment which included sequences encoding the t-PA presequence through amino acid 203. This fragment was ligated with the vector fragment of SmaI/EcoRI digested M13mp10RF, the replicative form M13 phage vector (see, e.g., Messing et al, Third Cleveland Symposium on Macromolecules Recombinant DNA, Editor A. Walton, Elsevier, Amsterdam (1981)). The intermediate plasmid, pPA-N44intA, was thus a replicative form of M13 phage which included the portion of the t-PA gene from which the codons for amino acids 1–44 were to be removed by site-directed deletion mutagenesis.

To perform the mutagenesis, an oligonucleotide primer was prepared by a method such as the phosphotriester method of Crea et al., Proc. Natl. Acad. Sci. (U.S.A.) 75, 5765 (1978). The primer employed to prepare a des (1–44) mutant was as follows:

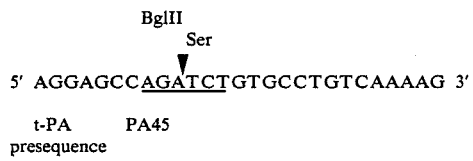

As will be appreciated, the ten 5' nucleotides of this primer encode presequence amino acids =3 to −1 (gly-ala-arg), whereas the seventeen 3' nucleotides encode amino acids 45 through 49 (SER-VAL-PRO-VAL-LYS). Note that the "TCT" codon was employed for serine-45 in order to retain the BglII site.

Approximately 200 mg of the synthetic oligonucleotide was phosphorylated for 30 minutes at 37° C. in 30 μl of 50 mM-Tris-HCl, pH 7.5, 10 mM MgCl$_2$, 10 mM dithiothreitol, 1 mM ATP containing about 8 U of T4 polynucleotide kinase. For heteroduplex formation, about 50 ng single-stranded pPA-N44intA was heated to 95° C. (10 min), and slowly cooled to room temperature (30 min), then to 4° C., in about 40 μl 10 mM Tris-HCl, pH 7.5, 10 mM MgCl$_2$, 1 mM dithiothreitol containing 100 ng of the phosphorylated primer. Primer extension was started by the addition of 10 μl ligase buffer containing 2 mM ATP, 0.25 mM each of dGTP, dCTP, dATP, dTTP, 5 U of E. coli polymerase I large (Klenow) fragment and 400 U of T4 DNA ligase. After 1 hour at 15° C. the reaction mixture was used to transform JM101 cells.

Transformation was performed by mixing all of the ligation mixture with 200 μl of competent JM101 cells, followed by incubation on ice for 30' and 5' at 37° C. Then 3.5 ml 2YT top agar at 55° C. was mixed with 200 μl of the phage-saturated cells, 10 μl IPTG (200 mM) and 50 μl X gal and after addition, the cells were plated onto Petri dishes containing 2YT with no drugs.

Colorless plaques were picked and transferred to a microtiter dish containing 100 μl 2YT medium. The inoculated microtiter fluids were stamped on 15 cm diameter LB agar plates overlayed with a lawn of 600 μl JM101 cells in 8 ml 2YT top agar and incubated overnight at 37° C. The formed plaques were transferred to a nitrocellulose disc by physical contact for 1 min. The nitrocellulose disc was treated with 0.5M NaOH, 1.5M NaCl for 3 min and washed twice with 3M NaCl-0.5M Tris-HCl pH 7.5 for 15 min and then with 2X SSC for 15 min. Prehybridization mix contains 10 mM Tris pH 7.5, 5 mM EDTA, 0.9M NaCl, IX Denhardt 0.5 percent NP40, 100 μM ATP, 1 mM sodium pyrophosphate, 1 mM sodium phosphate and 50 μg/ml E. coli tRNA. 1 X Denhardt's contains per liter 200 mg Ficoll, 200 mg polyvinylpyrrolidone, 200 mg bovine serum albumin (BSA; fraction V). The disc was baked at 80° C. in vacuo for 90 min. The disc was then incubated for 3 hrs with 6 ml prehybridization fluid in a Petri dish followed by addition of $5 \times 10^6$ cpm labeled primer and hybridized overnight. Selective washing of the disc was performed with 0.4X SSC at 49° C. and after air-drying the disc was exposed to X-ray film. Positively hybridizing clones were further analyzed by dideoxy sequencing. See Adelman, supra. From the positive colonies, a recombinant plasmid, designated pPA-N44intA delta, was selected which contained the proper deletion.

In order to replace the mutant gene sequence from the M13 phage into proper expression context into the DHFR-containing expression vector, plasmid pPADHFR-6 was digested separately with BglI/KpnI, to isolate the large fragment encoding the DHFR gene, and BstXI/KpnI, to isolate a 2240 base fragment encoding the 3' end (amino acids 45-527) of natural t-PA. A 400 base fragment bearing the N44 (des 1.44) mutation was isolated from pPA.N44intA delta by digestion with BglII/BstXI and ligated together with the two fragments derived from pPADHFR.6. The product of this ligation, designated CVSVPA.N44 D22, was thus a copy of the parental plasmid pPADHFR-6, except having codons encoding amino acids 1–44 removed.

(3) Plasmid pPADHFR-6 2C9

Plasmid pPADHFR.6 2C9 was prepared as described, for example, in U.S. Ser. No. 07/071,506, filed July 9, 1987 and its parents - see supra. In summary, human t-PA DNA was obtained from plasmids pPADHFR-6 (also designated pETPFR) and pA2-5E10. The preparation of these two t-PA plasmids is described in European Patent Application Publication No. 093619, supra.

Plasmid pA25E10 contains sequences coding for the last 508 amino acids of the t-PA gene and 772 base pairs of the 3' untranslated region. This plasmid was digested with SacI and BglII to produce a 744 base pair fragment which was isolated by standard methods as previously described. This fragment contains the codons for t-PA amino acids 411 through 527 and includes part of the 3' untranslated region.

Plasmid pPADHFR-6 contains the entire structural gene for t-PA and part of the 3' untranslated region. This plasmid was digested with SacI and BglII to produce a 1,230 base pair fragment which was isolated. This fragment contains codons for the first 410 amino acids of the mature form of t-PA.

These fragments were ligated together using standard methods and digested with BglII. A 1,974 base pair fragment containing codons for the entire mature t-PA sequence plus part of the 3' untranslated region was isolated. Double stranded M13mp8, (Messing, supra.) was digested with BamHI and annealed to the BglII digested t-PA to form M13mp8PABglII. *E. coli* JM 101 cells (ATCC No. 33876) were transformed with the double stranded replicative form of M13mp8PABglII. The single stranded and double stranded (RF) forms of M13mp8PABglII may be isolated from *E. coli* JM 101 cells infected with this phage. The single stranded form was used for the site specific mutagenesis of t-PA.

The human t-PA structural gene was modified by site specific mutagenesis to express t-PA with amino acid substitution at the appropriate various position. A synthetic oligonucleotide was prepared such as by the solid phase phosphotriester method of Crea et al. (supra.). Among the synthetic primers that were prepared and used for such site specific mutagenesis was:

Primer 2C9                         Glu
DNA Sequence   G CCT CAG TTT GAA ATC AAA GGA G The procedure described hereinafter, was used to generate different t-PA clones containing the mutated sequence of the synthetic primers. The general method used is that of Adelman (supra.), incorporated herein by reference. For example, 3M13RF2C9 was generated by the use of the above primer. Purified M13 RF DNA from the mutated t-PA gene was prepared from *E. coli* JM101 cells. Subsequently, DNA fragments containing the mutated t-PA DNA sequence were used to construct expression vectors for the mutated t-PA.

50 ng of a synthetic oligonucleotide was phosphorylated for 30 min at 37° C. in 10 μl of 50 mM Tris-HCl pH 7.5, 10 mM MgCl$_2$, 10 mM dithiothreitol, 1 mM ATP containing 8 U of T4 polynucleotide kinase. For use as a probe, 400 ng of the synthetic oligonucleotide was phosphorylated as above except that ATP was replaced with 60 mCi [$\gamma^{32}$-P]-ATP (3000 μCi/mmol) resulting in approximately 50 to 60×10$^6$ cpm/400 ng of 24-mer. For heteroduplex formation, 10 ng single stranded M13mp8PABglII was heated to 95° C. (10 min), and slowly cooled to room temperature (30 min) in 40 μl 10 mM Tris-HCl pH 7.5, 10 mM MgCl$_2$, 1 mM dithiothreitol containing 10 ng of the phosphorylated primer and 50 ng of EcoRI-digested M13mp8PABglIIRF large fragment. Primer extension was started by the addition of 10 μl ligase buffer containing 2 mM ATP, 0.25 mM each of dGTP, dTTP, dCTP and dATP, 5 U of *E. coli* DNA polymerase I large fragment and 400 U of T4 DNA ligase. After 1 hr at 12° C. the reaction mixture was used to transform *E. coli* JM101 cells.

Transformation was accomplished by mixing 10 μl of the ligation mixture with 200 μl of competent JM101 cells, followed by incubation for 30 min on ice and 5 min at 37° C. Then 3.5 ml 2YT top agar at 55° C. was mixed with 200 μl saturated JM101 cells, 10 μl IPTG (200 mM) and 50 μl X gal and after addition of the transformed cells plated 9 cm on Petri dishes containing LB with no drugs.

Colorless plaques were picked and transferred to a microtiter dish containing 100 μl 2YT medium. The inoculated microtiter fluids were stamped on 15 cm diameter LB agar plates overlayed with a lawn of 600 μl JM101 cells in 8 ml 2YT top agar and incubated overnight at 37° C. The formed plaques were transferred to a nitrocellulose disc by physical contact for 1 min. The nitrocellulose disc was treated with 0.5M NaOH, 1.5M NaCl for 3 min and washed twice with 3M NaCl-0.5M Tris-HCl pH 7.5 for 15 min and then with 2X SSC for 15 min. Prehybridization mix contains 10 mM Tris pH 7.5, 5 mM EDTA, 0.9M NaCl 1 X Denhardt 0.5 percent NP40, 100 μM ATP, 1 mM sodium pyrophosphate, 1 mM sodium phosphate and 50 μg/ml *E. coli* tRNA. 1X Denhardt's contains per liter 200 mg Ficoll, 200 mg polyvinylpyrrolidone, 200 mg bovine serum albumin (BSA; fraction V). The disc was baked at 80° C. in vacuo for 90 min. The disc was then incubated for 3 hrs with 6 ml prehybridization fluid in a Petri dish followed by addition of 5×10$^6$ cpm labeled primer and hybridized overnight. Selective washing of the disc was performed with 0.4X SSC at 49° C. and after air-drying the disc was exposed to X-ray film. Positively hybridizing clones were further analyzed by dideoxy sequencing. See Adelman, (supra.).

Vector fragment designated as fragment 1 was obtained by isolating the large fragment generated by digestion of pPADHFR-6 with BglII and BstEII. A fragment designated as fragment 2 was obtained by isolating the 400 base pair t-PA fragment obtained from the digestion of pPADHFR-6 with BglII and BstXI. A 1,141 base pair t-PA fragment containing the desired mutations (fragment 3) was obtained by digesting RF DNA from the mutant t-PA clones (supra) with BstXI and BstEII. Fragments 1 and 2 were ligated with each fragment 3. The DNA mixtures were used to transform *E. coli.* From each of the transformants, the respective eukaryotic expression vectors were obtained, for example: pPADHFR-6 2C9.

(4) Final Construction of p1154

Plasmid pETPFR was digested with the restriction enzymes BglII and ApaI and the fragments fractionated by agarose gel electrophoresis. The 6.0 kb fragment containing the t-PA preprocoding region, the SV40 early promoter, β-lactamase, and DHFR genes was cut out from the gel and electroeluted.

Plasmid pCVSVPA-N44 D22 was digested with BglII and ScaI, the fragments fractionated by acrylamide gel electrophoresis, and the band containing the 0.63 kb fragment (representing the coding sequences for the growth factor, kringle one and kringle two [partial] domains of t-PA) was cut out and electroeluted.

Plasmid pPADHFR-6 2C9 was digested with ScaI and ApaI, and the 0.63 kb fragment containing the coding sequences for kringle two (partial) and the protease (with the Glu 275 mutation) domains was purified by acrylamide gel electrophoresis and electroelution.

The three thus isolated, purified fragments were incubated in the presence of T4 DNA ligase and rATP to produce the plasmid p1154, containing sequences coding for a t-PA molecule lacking residues 1–44 (finger domain deletion) and incorporating an Arg 275 →Glu mutation (single chain mutant). See FIG. 11.

EXAMPLE V

Preparation of Other Domain Deletion Variants of t-PA

The construction of plasmid pCVSVPA-N44 D22 is described in detail supra. in connection with the description of the preparation of plasmid p1154.

Likewise, site directed mutagenesis experiments are discussed in detail supra. in connection with the preparation of plasmid pPADHFR-6 2C9.

The des 44–84 growth factor domain deletion, des 92–179 Kringle 1 domain deletion, and des 174–261

Figure 11:
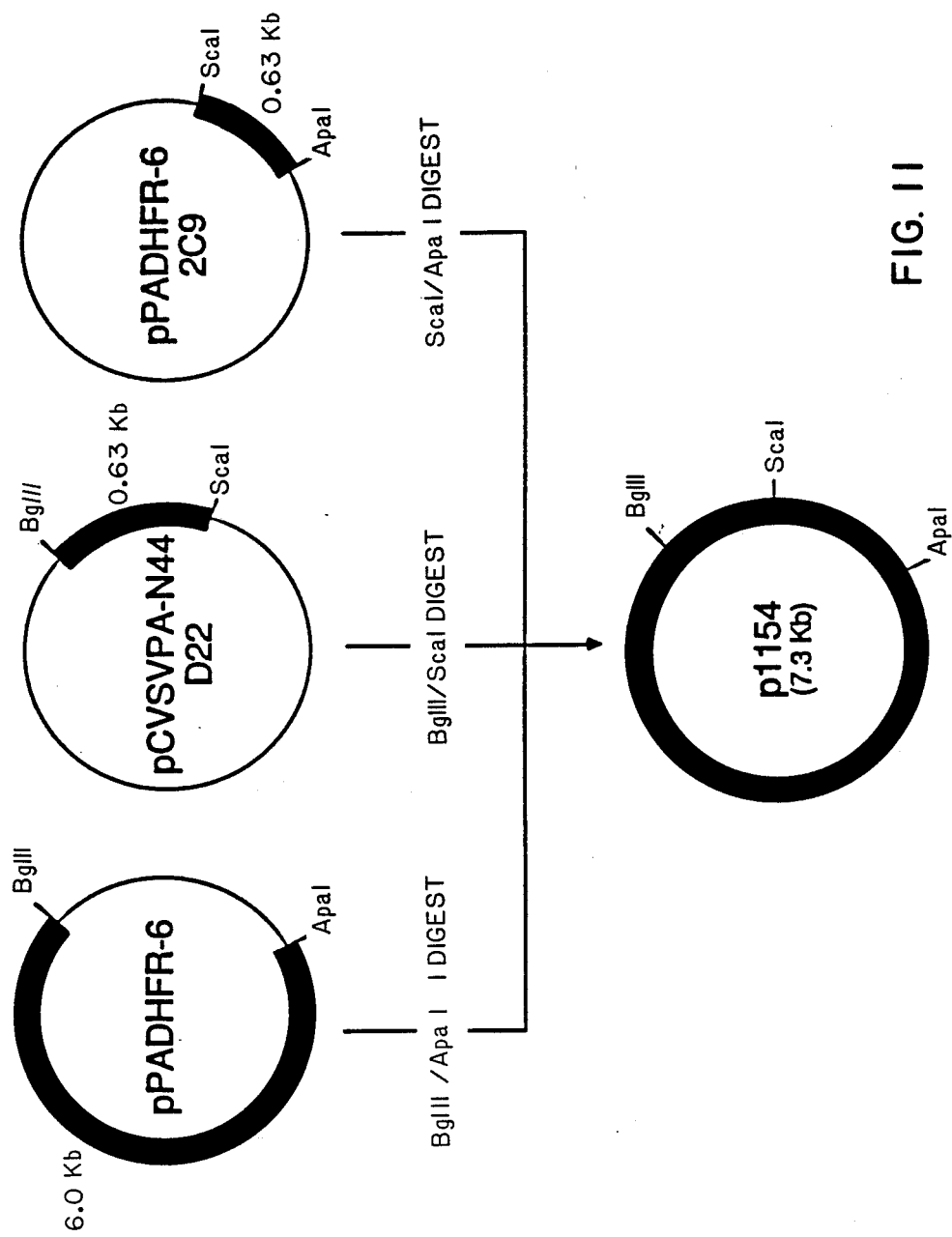
FIG. 11 is a schematic representation of how plasmid p1154 can be prepared and demonstrates also a partial restriction mapping thereof.
Figure 13:
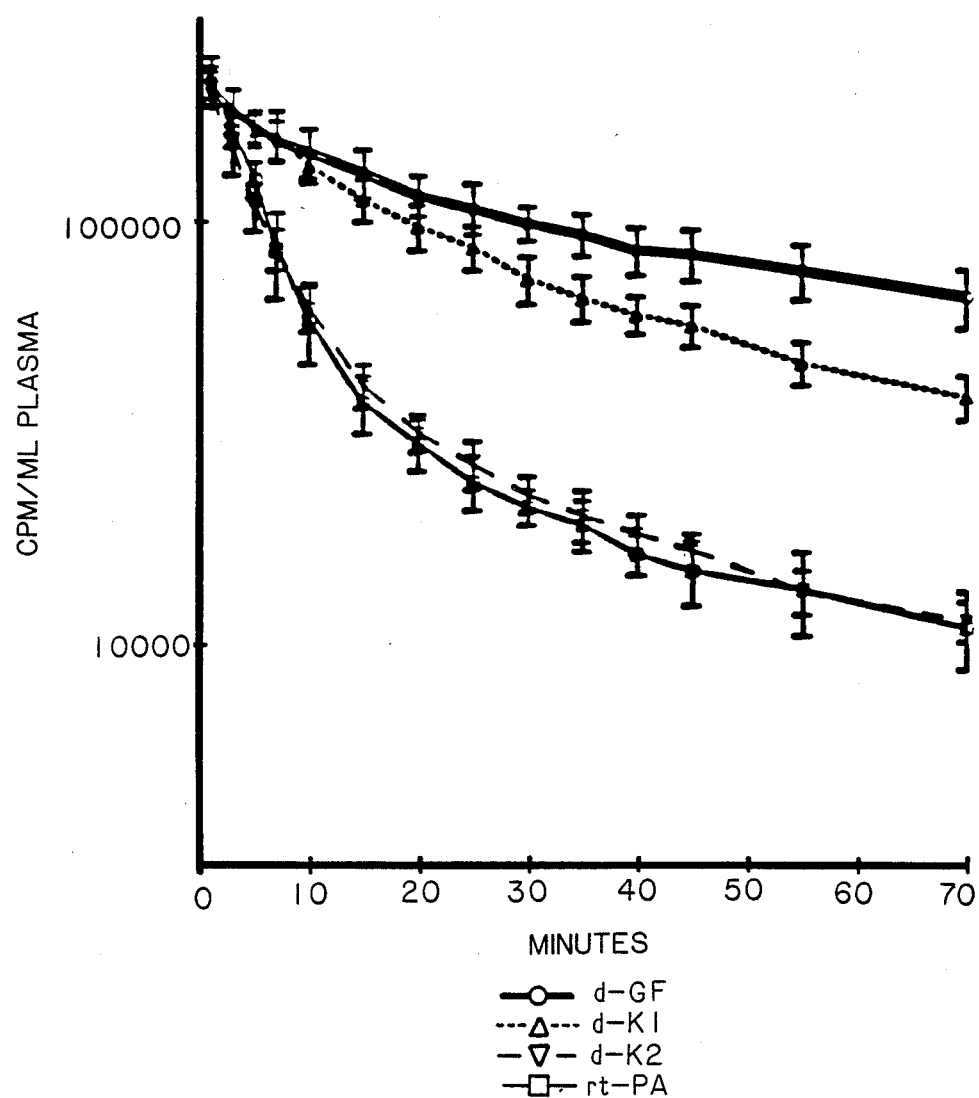
FIG. 13 shows the pharmacokinetic profiles, in rabbits, of the various domain deletion mutants: growth factor deletion, des 44-84 ("d-GF"); Kringle 1 deletion, des 92-179 ("d-K1"); Kringle 2 deletion des 174-261 ("d-K2"); and native t-PA ("rt-PA") as a control.

Kringle 2 domain deletion were also made by site-directed mutagenesis using the following oligonucleotides:

des 44-84  GCAGGGCACAGTGCGAAATAGATACTCGAGCCACGTGCTACG des 92-179  TGTGAAATAGATACTCGAGCCACGTGCTACTTTGGGAATGGA-
TCCGCCTACCGTGGC des 174-261  TTCTGCAGCACCCCTGCCTGCTCCACCTGCGGCCTG and these used to prepare expression plasmids in a manner analogous to the des 1-44 construction supra, except that mutagenesis was performed on the 1.4 kb BglII/ApaI fragment (in a single stranded vector) containing the bulk of the t-PA coding sequences—See FIG. 11. Also in a manner analogous to the des 1-44 construction, the des 44-84 and des 92-179 mutations could, in principle, also be isolated on BglII/ScaI fragments and joined to the Glu275 mutations and the t-PA C-terminal coding sequences on the 0.63 kb ScaI/ApaI fragment, thus creating plasmids similar to p1154 as described supra. These plasmids are used to transfect appropriate cells and the corresponding t-PA variant produced as described supra.

EXAMPLE VI

Demonstration of in Vivo Protease Amidolytic Activity of des (1-44) t-PA

The activity of des (1-44) t-PA in a protease amidolytic assay was compared to that of natural t-PA using the S-2288 paranitroanilide chromogenic substrate (Helena Labs). The S-2288 paranitroanilide substrate provides a direct measurement of protease amidolytic activity. The kinetic constants for t-PA and des 1-44 t-PA were determined with the S-2288 substrate using an H-P diode array spectrophotometer (HP8451-A). Hydrolysis of the substrate was measured continuously at two substrate concentrations (1.0 mM and 0.1 mM) while the protein concentrations were held constant at 23 nM in a buffer composed of 0.05M Tris-HCl, 0.12M NaCl, 0.01% Tween 80, pH 7.4. Using the differential form of the Michaelis-Menten equation and a non-linear regression the Km and Vmax were calculated from the curves of the progress of the reaction.

Both des 1-44 t-PA and normal sequence t-PA exhibited similar specific activity using the small synthetic S-2288 substrate, H-D-isoleucyl-L-prolyl-L-arginine p-nitroanilide. As shown in Table 1, the kcat and Km of the two enzymes were within experimental error of each other, which indicated that the protease portion of the molecule has normal function and that the finger domain has no effect on the hydrolysis of small molecular weight substrates.

TABLE 1

KINETIC CONSTANTS FOR WILD TYPE t-PA AND DES 1-44 t-PA with S-2288

| | $k_{cat}$ (sec$^{-1}$) | $K_m$ (mM) | $k_{cat}/K_m$ (sec$^{-1}$mM$^{-1}$) |
|---|---|---|---|
| Wild type t-PA | 17.9 | 0.33 | 54.2 |
| Des 1-44 t-PA | 17.1 | 0.28 | 61.1 |

EXAMPLE VII

Demonstration of in Vitro Plasminogen Activation by des (1-44), t-PA

The ability of t-PA to activate plasminogen can be measured in an in vitro assay by preincubating t-PA and plasminogen and then adding the plasmin specific substrate H-D-valyl-H-leucyl-H-lysine. p-nitronilide (S-2251). The maximum rate of this reaction is observed in the presence of fibrin(ogen) or fragments of fibrin(ogen) which act as stimulators of the reaction.

The plasmin specific substrate S-2251 was used in a two-stage assay to measure the ability of the sample to activate plasminogen. Fibrin clots were made by incubating the sample with 0.02 ml of a 20 mg/ml fibrinogen solution with 1U of thrombin in a total volume of 0.12 ml of 0.05M Tris-HCl, 0.12M NaCl, 0.01% Tween 80, pH 7.4 for 30 min. at 37° C. Alternatively, the thrombin could be omitted and fibrinogen used as the stimulator. Glu-plasminogen solution, 0.03 ml of a 2.1 mg/ml solution, was then added. After 10 min at 37° C., 0.35 ml of 2.86 mM S-2251 in 0.037M Tris, 0.86 NaCl, 0.007% Tween 80, pH 7.4) were added. This mixture was incubated for five minutes then the reaction was stopped by the addition of 0.1 ml of 50% glacial acetic acid. Absorbance at 405 nm was measured. The activity was expressed as the change in absorbance per nanogram per minute in the presence of substrate.

The assay was run as described, along with an additional set of samples which did not contain fibrin clots. The stimulation is the ratio of the specific activity of the sample containing fibrin and the specific activity of the sample not containing fibrin.

In various assays (see Table 2 and FIG. 4), the maximum specific activity obtained with des 1-44 t-PA in the presence of fibrin was slightly greater than 50% of the rate obtained with normal sequence t-PA. The activity of both t-PA and des (1-44) t-PA increased about 50-fold in the presence of fibrin. In Table 2, the value for "stim" compares the stimulation seen in the presence of fibrinogen versus no fibrinogen.

TABLE 2

| +Fgn rel | Stim |
|---|---|
| With Fibrinogen | |
| 100% | 100 |
| 50% | 70.2 |
| With Fibrin Clots | |
| 100% | 100 |
| 56% | 80.4 |

In order to further compare the ability of des 1-44 t-PA to activate plasminogen in the presence of fibrin(ogen), it was compared to t-PA in an assay which measures the ability of t-PA and saturating plasminogen to lyse a fibrin clot. In this assay, des 1-44 t-PA exhibited only 35% of the activity observed with normal t-PA (Table 3). These results suggest that there may be a defect in the ability of des 1-44 t-PA to interact properly with fibrin.

TABLE 3

| ACTIVITY OF r-PA and des 1-44 t-PA | | |
|---|---|---|
| | t-PA des | 1-44 t-PA |
| Clot lysis (relative units) | 1.0 | 0.18 |

The binding of des 1-44 t-PA to fibrin was monitored using a modification of the method of Rijken et al. (1982 J. Biol. Chem., 257:2920). Samples were mixed with various concentrations of human plasminogen-free fibrinogen, in the presence of 1 mg/ml human serum albumin (from J E M Research, Inc., Kensington, Md.) to prevent nonspecific adsorption. The total reaction volume was 1 ml and the buffer was composed of 0.05M Tris-HCl, 0.12M NaCl, 0.01% Tween 80, pH 7.4. One unit of thrombin (from Sigma Chemical Co., St. Louis, Mo.) was added and the mixtures were clotted for one hour at 37° C. The clots were physically removed by centrifugation at 10,000 rpm for 5 min and an aliquot of the supernatant was then assayed for remaining t-PA content by either an activity assay or an ELISA.

Figure 5:
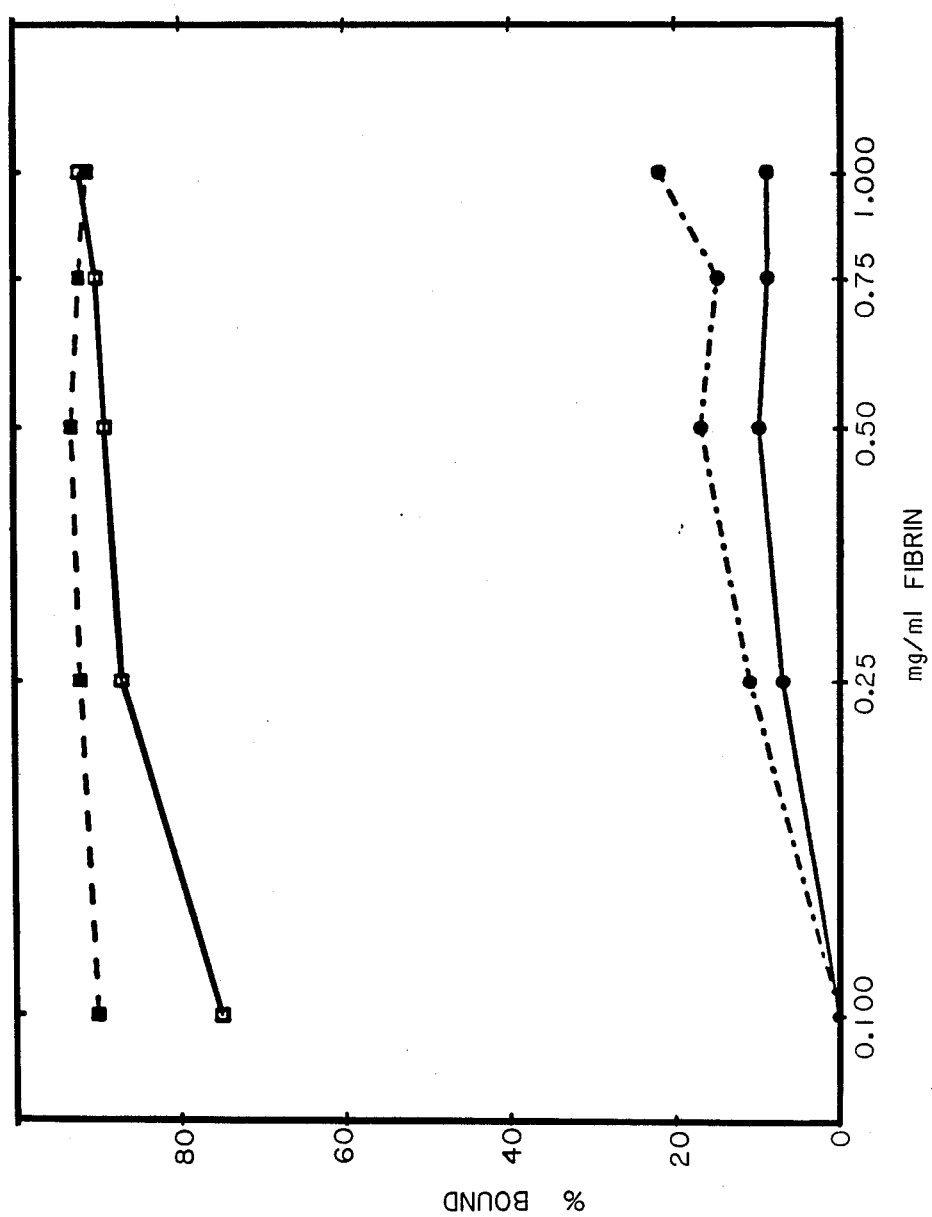
FIG. 5 compares the fibrin-binding activity of natural t-PA (intact fibrin,□, and plasmin-degraded fibrin,■) to des (1-44) t-PA (intact fibrin, O, and plasmin degraded,●.

The results are shown in FIG. 5. As will be appreciated, the des (1-44) exhibited a much reduced ability to bind fibrin. Although the binding to fibrin was so weak that a dissociation constant could not be obtained, it was estimated that the dissociation was at least 10 fold higher than that for natural t-PA ("RIK"). Thus, fibrin binding is not required in order to retain efficacy of the t-PA activity.

EXAMPLE VIII

In Vivo Clot Lysing Activity of Des (1-44) t-PA Versus Natural t-PA

An in vivo experiment was performed in rabbits to demonstrate the dose response of natural t-PA (designated RIK) versus the Des (1-44) t-PA variant. Thrombolytic activities were determined in rabbits using a extracorporeal shunt which contained a thrombus labeled with I-125 fibrinogen. Lysis was measured by the disappearance of radioactivity, measured by an external sodium iodine crystal. The wild type t-PA was given as a 10% bolus with the remainder of the dose infused over the following 90 min. The des (1-44) t-PA was tested at single dose of 0.064 mg/kg using a 0.03 mg/kg bolus followed by an infusion of 0.034 mg/kg for 90 min. All lysis was determined at the end of the 90 min. infusion.

Figure 6:
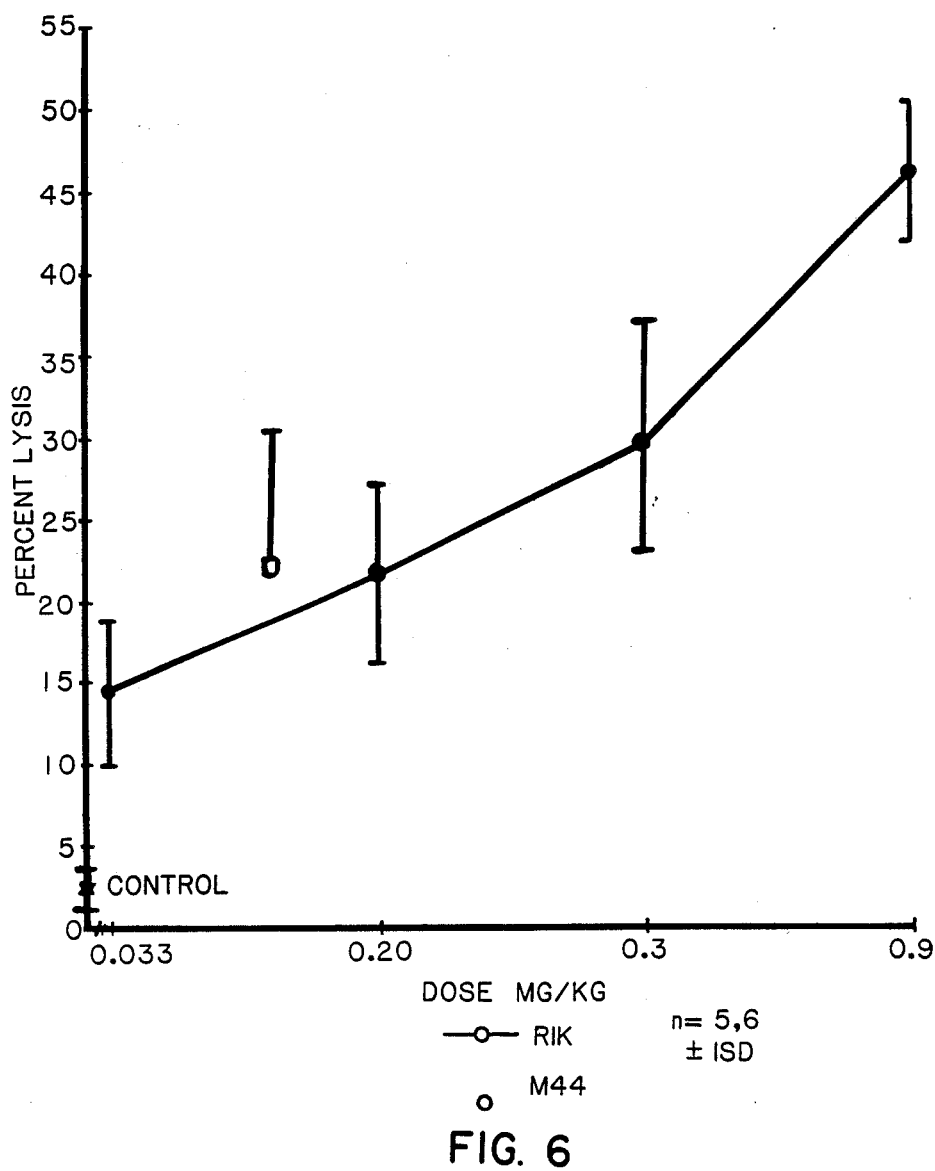
FIG. 6 compares the in vivo thrombolytic activity of des (1-44) t-PA (N44) to natural t-PA (RIK) in rabbits (n=6, 5+S.D., respectively).

As can be seen in FIG. 6, in an in vivo assay, the des (1-44) t-PA variant exhibited surprisingly high clot lysing activity, within the standard error of natural t-PA. This finding was particularly surprising in light of the in vitro assay results wherein the lysis activity reflected a lower lytic activity for the N44 variant. However, such in vitro experiments failed to take into account the increased half-life of the variant.

Figure 7:
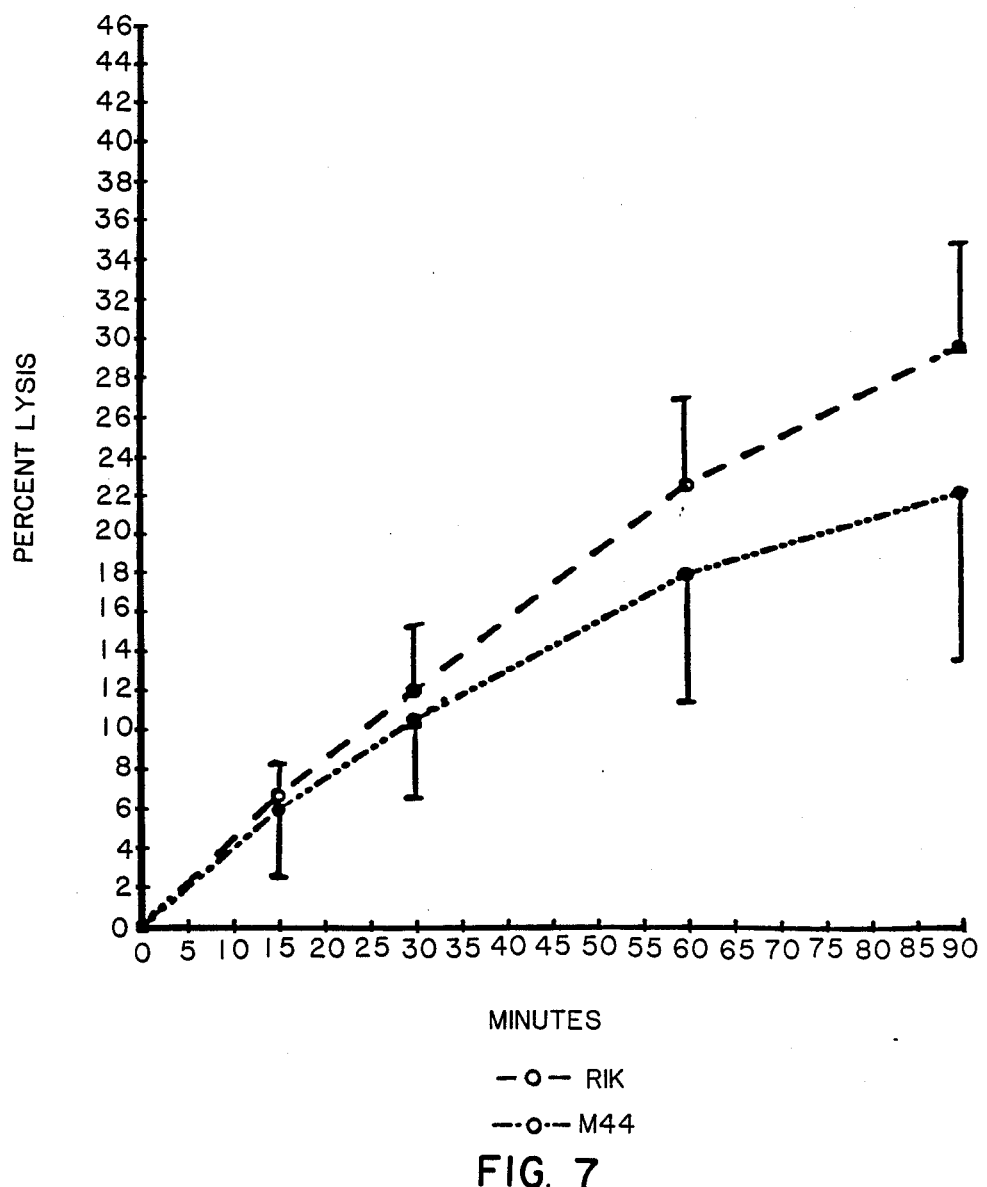
FIG. 7 compares the lysis rate of natural t-PA (o) to the des (1-44) t-PA variant (●), at a dose of 0.3 and 0.064 mg/kg, respectively, given as a 10% bolus, followed by infusion of the remainder over 90 minutes.

In a second type of assay, the two species were compared in terms of percent lysis versus time. The results are shown in FIG. 7 wherein comparable lysis rates were graphed for the 0.3 mg/kg wild type rt-PA dose and for the 0.064 mg/kg des (1-44) rt-PA. As will be appreciated, the activity with time of the des (1-44) variant (N44) closely paralleled the activity of natural t-PA (RIK).

Figure 8:
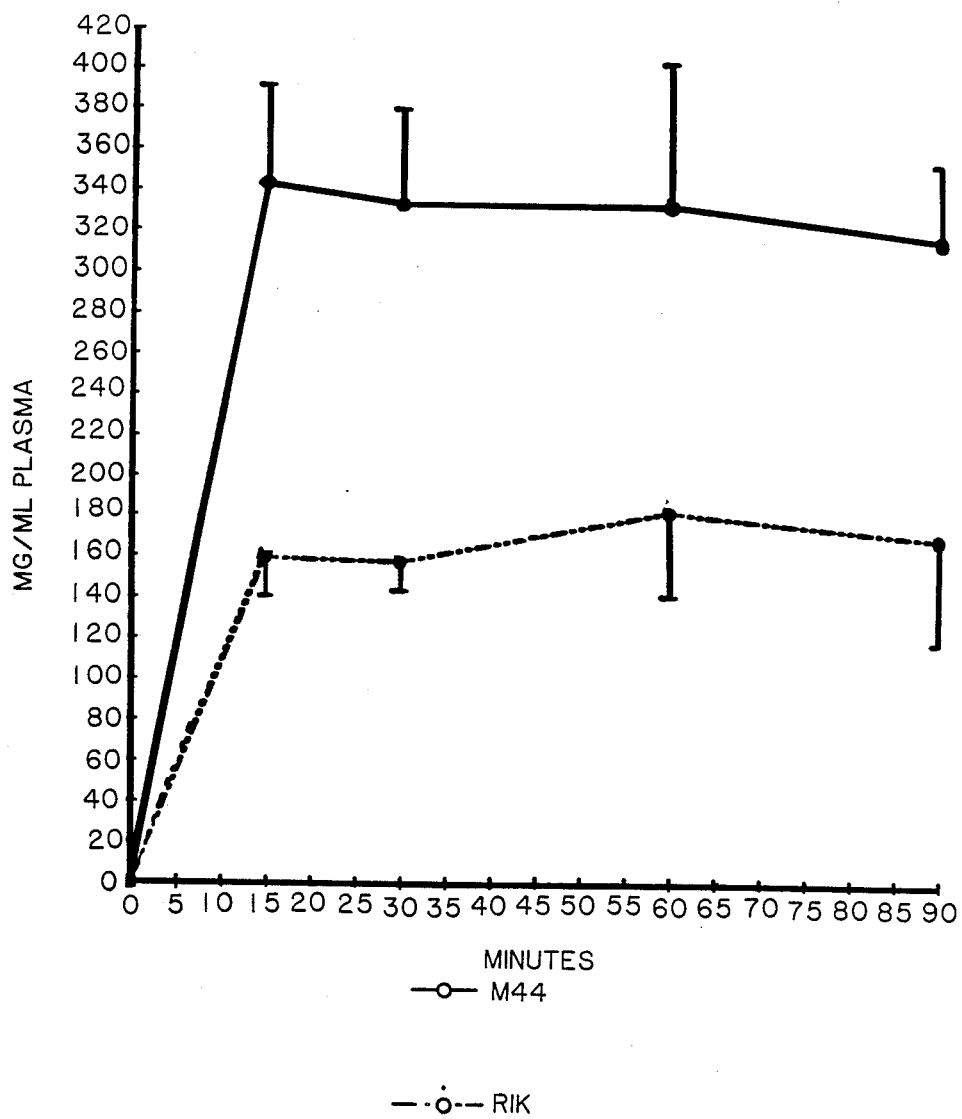
FIG. 8 compares the time course of the plasma concentration resulting from an administration of 0.3 natural or 0.064 mg/kg N44 variant, given as a 10% mg/kg bolus with the remaining infused over a 90 min. time course.

In FIG. 8 is shown the time course of the plasma concentration of the two forms of rt-PA from the foregoing study. Concentrations were determined by a polyclonal ELISA which detects both forms of rt-PA with equal activity. Blood samples were collected on EDTA and an irreversible inhibitor of rt-PA, D-Phe-Pro-Arg-chloromethyl ketone, was added; this inhibitor blocks in vitro formation of t-PA complexes with plasma protease inhibitors. These complexes have significantly decreased immunoreactivity. As will be appreciated, the N44 variant generated a much higher plasma concentration than natural t-PA with a much lower initial and total dose.

EXAMPLE IX

Pharmacokinetic Studies

Comparative pharmacokinetic studies were performed in rabbits. I-125 labeled test t-PA, either wild type or N44 variant, 5 uCi/kg with a specific activity of 5 to 10 uCi/ug, and carrier wild type t-PA, 1.0 mg/kg, were coinjected, serial blood samples were collected, plasma prepared and the TCA (trichloroacetic acid) precipitable counts were determined at each time point. TCA precipitation was used in order to remove any small metabolites which appear at later times due to degradation of t-PA by the liver. The plasma concentration time curve for rt-PA was fit to a biexponential equation $C = A\exp(-\alpha Xt) + B\exp(-\beta Xt)$. The curve for the des (1-44) rt-PA was fit to a monoexponential equation $C = A\exp(-\alpha Xt)$. The clearance (Cl) was calculated by the formula $Cl = DOSE/AUC$, where AUC is the area under the plasma concentration time curve.

Figure 9:
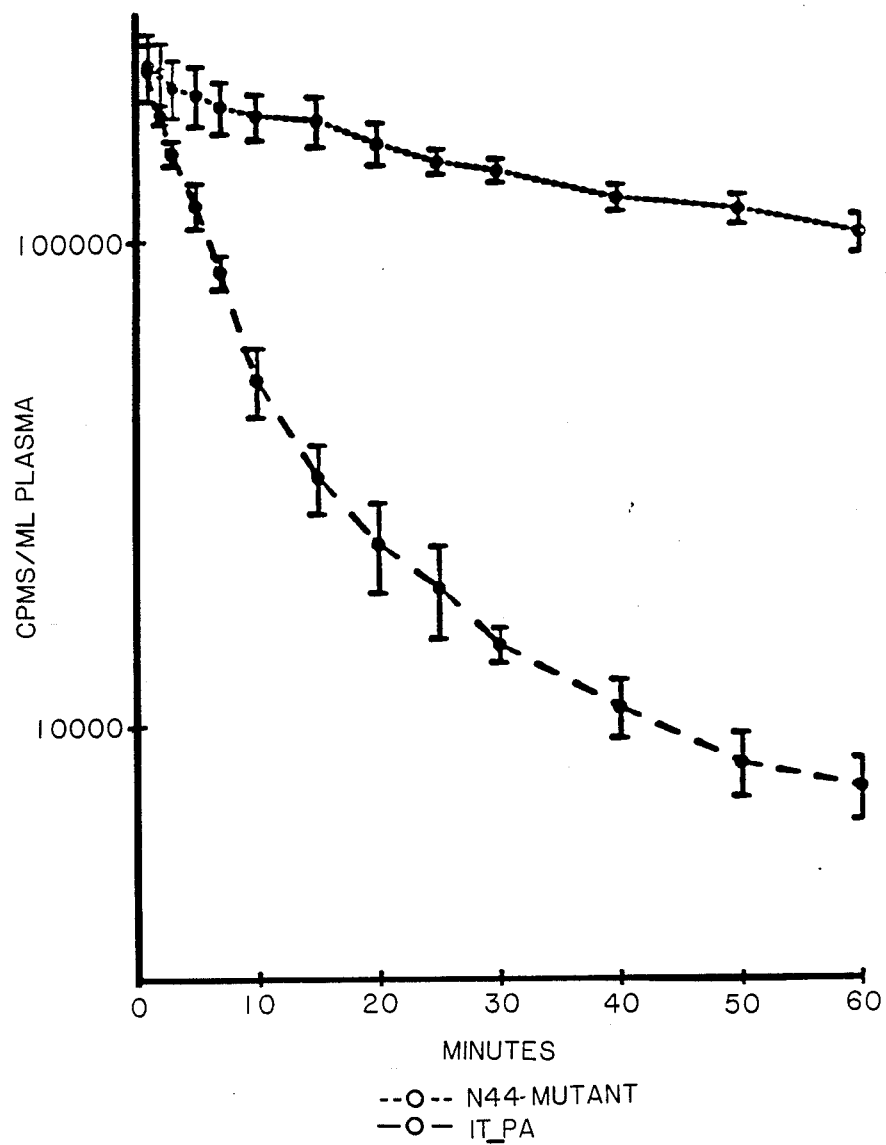
FIG. 9 compares the pharmacokinetics of N44 to natural t-PA (rt-PA), using non-radioactive rt-PA as the carrier.

As can be seen from the results obtained, displayed below in Table 4 and plotted in FIG. 9, in a rabbit test system, the natural t-PA sample, rt-PA, exhibited a clearance rate of about 8.4 ml/min/kg, with a standard deviation of about 0.92, and a half-life (t1/2a) of about 3.1 minutes, with a standard deviation of about 0.55.

TABLE 4

| PHARMACOKINETIC PARAMETERS OF AN I.V. BOLUS DOSE OF I-125 rT-PA, IN RABBITS DOSE = 5 uC/kg I-125 rT-PA COINJECTED WITH 1 mg/kg COLD rT-PA | | | | | | |
|---|---|---|---|---|---|---|
| | #A | #C | #E | #G | MEAN | S.D. |
| B0 | 30144.320 | 32920.033 | 27005.306 | 31340.936 | 30352.649 | 2504.415 |
| t1/2b | 33.236 | 23.987 | 31.782 | 26.467 | 28.868 | 4.365 |
| rsq | 0.973 | 0.963 | 0.997 | 0.959 | 0.973 | 0.017 |
| A0 | 247990 | 306059 | 255904 | 290852 | 275201 | 27748.868 |
| t1/2a | 3.716 | 2.645 | 3.334 | 2.575 | 3.067 | 0.552 |
| rsq | 0.999 | 0.991 | 0.983 | 0.971 | 0.986 | 0.012 |
| AUC × 10-6 | 26.609 | 21.106 | 23.505 | 21.128 | 23.087 | 2.604 |
| AUMC × 10-6 | 789.510 | 452.925 | 637.710 | 525.828 | 601.493 | 146.583 |
| VDSS ml/kg | 209.553 | 197.899 | 232.427 | 213.466 | 213.336 | 14.342 |
| CL ml/min/kg | 7.063 | 9.222 | 8.567 | 8.577 | 8.357 | 0.916 |

However, with the des (1-44) variant, N44, as shown below in Table 5 and in FIG. 9, a clearance rate of about 0.48 ml/min/kg (S.D. —0.02) and a half-life of about 53.7 minutes (S.D. =6.58), was observed.

TABLE 5

PHARMACOKINETIC PARAMETERS OF A BOLUS DOSE OF I-125 N-44, IN RABBITS DOSE = 5 uC/kg I-125 N44, COINJECTED WITH 1 mg/kg COLD rT-PA

|  | #b | #d | #f | #h | MEAN | s.d. |
|---|---|---|---|---|---|---|
| A0 | 234100 | 245900 | 183000 | 202300 | 216300 | 28870.000 |
| lambda0 | 0.014 | 0.015 | 0.011 | 0.012 | 0.013 | 0.002 |
| t1/2 | 50.220 | 46.310 | 60.740 | 57.370 | 53.660 | 6.575 |
| rsquare0 | 0.984 | 0.914 | 0.980 | 0.945 | 0.956 | 0.033 |
| AUC × 10-6 | 171.400 | 170.900 | 158.600 | 172.400 | 168.300 | 6.552 |
| AUMC × 10-6 | 12610.000 | 12050.000 | 13800.000 | 14740.000 | 13300.000 | 1205.000 |
| VDSS ml/kg | 34.540 | 33.200 | 44.190 | 39.890 | 37.960 | 5.060 |
| CL ml/min/kg | 0.470 | 0.471 | 0.508 | 0.467 | 0.479 | 0.019 |

Figure 10:
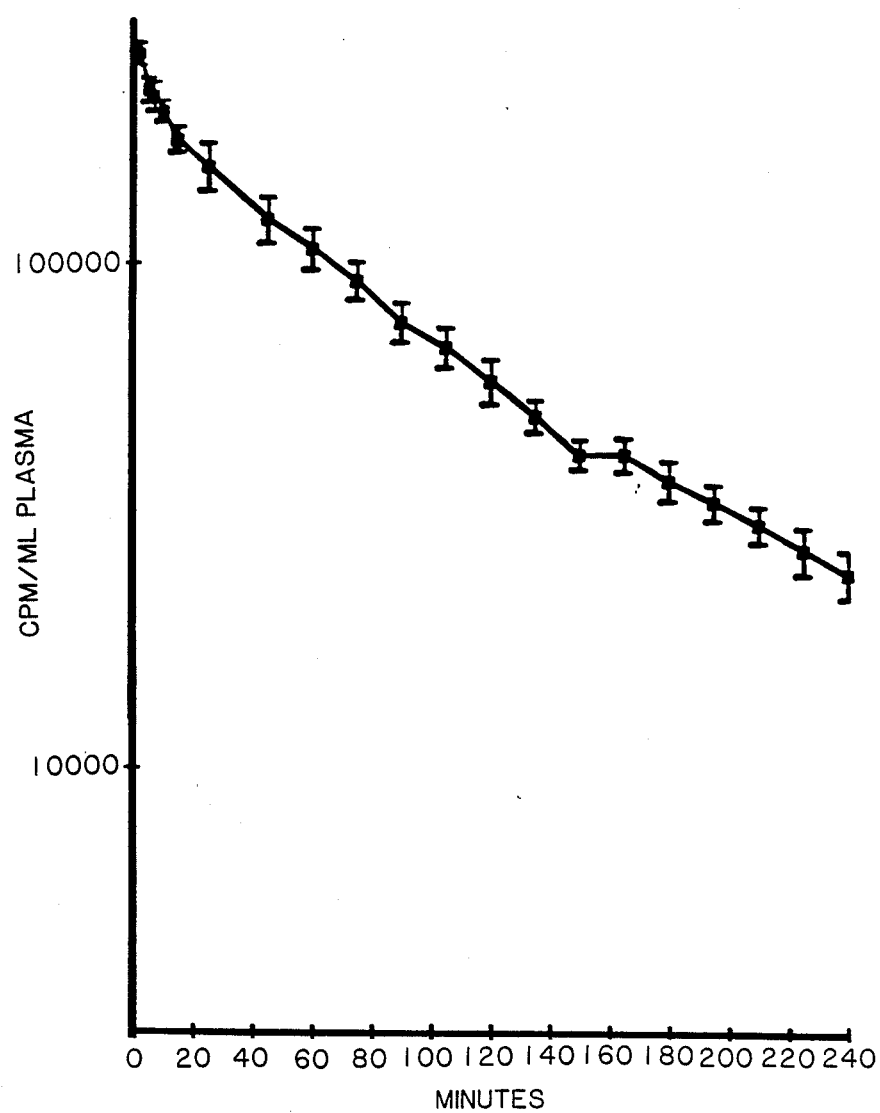
FIG. 10 displays the pharmacokinetics of N44, using N44 as the carrier.

Pharmacokinetic analyses were repeated as above except that, instead of using natural t-PA as carrier for the labeled N44 variant, the variant N44 (non-radioactive) itself was employed at a concentration of 1 mg/kg. The results are shown below in Table 6 and FIG. 10. As will be appreciated, using the N44 carrier a half-life of about 73.1 minutes (S.D.=1.22) was observed, with a clearance rate of about 0.42 ml/min/kg (S.D. —0.03).

TABLE 6

PHARMACOKINETIC PARAMETERS OF A BOLUS DOSE OF I-125 N-44, IN RABBITS DOSE = 5 uC/kg I-125 N44 COINJECTED WITH 1 mg/kg COLD N44

|  | #a | #b | #c | MEAN | s.d. |
|---|---|---|---|---|---|
| A0 | 197800 | 197000 | 221500 | 205400 | 13900.00 |
| lambda0 | 0.01 | 0.01 | 0.01 | 0.01 | 0.00 |
| t1/2 | 71.68 | 73.81 | 73.76 | 73.08 | 1.22 |
| rsquare0 | 0.98 | 0.97 | 0.98 | 0.98 | 0.01 |
| AUC × 10-6 | 200.10 | 205.10 | 233.70 | 213.00 | 18.14 |
| AUMC × 10-6 | 21470.00 | 22810.00 | 25870.00 | 23380.00 | 2258.00 |
| VDSS ml/kg | 47.17 | 47.72 | 41.68 | 45.52 | 3.34 |
| CL ml/min/kg | 0.44 | 0.43 | 0.38 | 0.42 | 0.03 |

Based on the foregoing clearance rates and half-lives observed in the rabbit test animals, it can be readily predicted that a similar or greater half-life, as well as a similar or lower clearance rate, will be obtained in man.

What is claimed is:

1. A method for providing a variant human t-PA protein exhibiting an enhanced plasma half-life or decreased clearance rate relative to natural t-PA, the method comprising the steps of:
   (a) obtaining a t-PA variant comprising t-PA devoid only of one or two domains selected from the group consisting of at least a portion of (1) the finger, (2) the growth factor and (3) the Kringle 1 domain;
   (b) comparing the pharmacokinetics of said t-PA variant with that of natural t-PA; and
   (c) selecting a variant t-PA so obtained which exhibits a longer plasma half-life or decreased clearance rate relative to natural t-PA.

2. The method of claim 1, wherein said t-PA variant comprises t-PA devoid only of the finger domain.

3. The method of claim 1, wherein said t-PA variant comprises t-PA devoid only of the growth factor domain.

4. The method of claim 1, wherein said t-PA variant comprises t-PA devoid only of the Kringle 1 domain.

5. The method of claim 1, wherein said t-PA variant comprises t-PA devoid only of amino acids corresponding to amino acid numbers 1 through 44 of natural t-PA.

6. The method of claim 1, wherein said t-PA variant comprises t-PA devoid only of amino acids corresponding to amino acid numbers 44 through 84 of natural t-PA.

7. The method of claim 1, wherein said t-PA variant comprises t-PA devoid only of amino acids corresponding to amino acid numbers 92 through 179 of natural tPA.

8. The method of any one of claims 2 to 7, wherein said t-PA variant additionally has Glu at amino acid 275.

9. The method of claim 1, wherein said t-PA variant is additionally a protease resistant one-chain variant.

10. The method of claim 1, wherein said variant is des 1-44 Glu 275 t-PA.

11. The method of claim 9, wherein said one-chain variant includes an amino acid other than arginine at position 275 as measured relative to natural t-PA.

12. A method for the preparation of a pharmaceutical t-PA preparation having an increased plasma half-life, or decreased clearance rate, relative to natural t-PA, the process comprising the steps of:
   (a) obtaining a t-PA variant comprising t-PA devoid only of at least a portion of the finger, and one of (1) at least a portion of the growth factor and (2) at least a portion of the Kringle 1 domain; and
   (b) formulating therapeutically effective quantities of said t-PA variant together with a selected diluent or carrier to provide a pharmaceutically acceptable preparation.

13. The method of claim 12, wherein said t-PA variant is additionally a protease resistant one-chain variant.

14. The method of claim 13 wherein said variant additionally has Glu at amino acid 275.

15. Des 1-44 Glu 275 t-PA.

* * * * *